United States Patent [19]

Suhadolnik et al.

[11] Patent Number: 5,643,889
[45] Date of Patent: Jul. 1, 1997

[54] CHOLESTEROL CONJUGATES OF 2'5'-OLIGOADENYLATE DERIVATIVES AND ANTIVIRAL USES THEREOF

[75] Inventors: Robert J. Suhadolnik, Roslyn, Pa.; Wolfgang Pfleiderer, Constance, Germany

[73] Assignee: Temple University-of the Commonwealth System of Pennsylvania, Philadelphia, Pa.

[21] Appl. No.: 306,274

[22] Filed: Sep. 14, 1994

Related U.S. Application Data

[63] Continuation-in-part of Ser. No. 849,865, Mar. 12, 1992, abandoned, which is a continuation-in-part of Ser. No. 613,848, Dec. 6, 1990, abandoned, which is a continuation-in-part of Ser. No. 204,659, Jun. 9, 1988, abandoned, which is a continuation-in-part of Ser. No. 144,602, Jan. 11, 1988, Pat. No. 4,859,768, which is a continuation of Ser. No. 629,660, Jul. 11, 1984, abandoned.

[51] Int. Cl.[6] .................... A01G 7/06; A61K 31/70
[52] U.S. Cl. .................... 514/44; 514/26; 514/46; 514/47; 514/61; 514/169; 536/5; 536/25.2; 47/58
[58] Field of Search ................ 514/44, 45, 46, 514/47, 26, 5, 169, 61; 536/4.1, 5, 22.1, 23.1, 25.2; 47/58

[56] References Cited

U.S. PATENT DOCUMENTS

| | | | |
|---|---|---|---|
| 4,464,359 | 8/1984 | Suhadolnik et al. | 514/47 |
| 4,859,768 | 8/1989 | Suhadolnik et al. | 536/25.2 |
| 4,924,624 | 5/1990 | Suhadolnik et al. | 47/58 |
| 4,981,957 | 1/1991 | Lebleu et al. | 536/25.2 |
| 5,108,921 | 4/1992 | Low | 435/240.1 |

FOREIGN PATENT DOCUMENTS 0 220 030   4/1987   European Pat. Off. .

OTHER PUBLICATIONS

G. Zon, "Pharmaceutical Considerations", Chapter 11 in *Oligodeoxynucleotides*, J. Cohen (ed.), CRC Press, Inc., Boca Raton, FL, pp. 233-247 (1989).

J. Goodchild, *Bioconjugate Chemistry* 1: 165-187 (1990).

Beaucage et al., *Tetrahedron* 49: 1925-1963 (1993).

*Primary Examiner*—James O. Wilson
*Attorney, Agent, or Firm*—Seidel, Gonda, Lavorgna & Monaco, P.C.

[57] ABSTRACT

A cholesterol-cordycepin conjugate having the formula

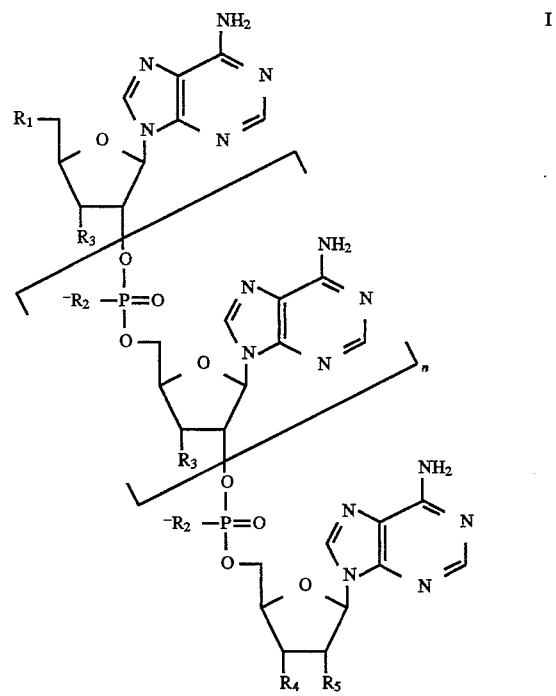

wherein:

n is an integer from 1 to 8; $R_1$ is selected from the group of consisting of T, T' and Y; T is

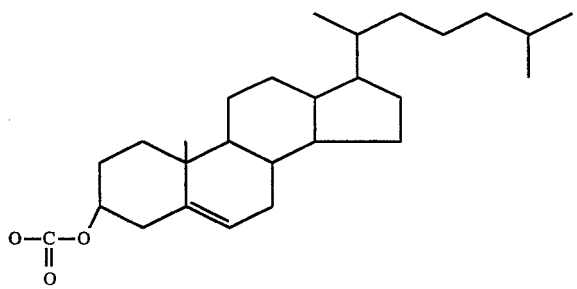

T' is

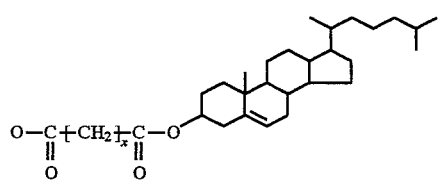

where x is an integer from 1 to 18; Y is

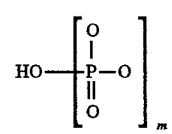

where m is zero, 1, 2, or 3; each $R_2$ is independently selected from the group consisting of oxygen and sulfur; each $R_3$ is independently selected from the group consisting of hydrogen and hydroxyl; $R_4$ is selected from the group consisting of hydrogen, hydroxyl and T or T'; $R_5$ is selected from the group consisting of hydrogen, hydroxyl and T or T'; provided that all $R_1$, $R_4$ and $R_5$ may not be T or T'; at least one $R_3$ is hydrogen or $R_4$ is hydrogen; and at least one of $R_1$, $R_4$ and $R_5$ must be T or T'; or a water soluble salt thereof. The compounds possess increased antiviral activity and/or metabolic stability.

16 Claims, No Drawings

CHOLESTEROL CONJUGATES OF 2',5'-OLIGOADENYLATE DERIVATIVES AND ANTIVIRAL USES THEREOF

CROSS-REFERENCE TO RELATED APPLICATIONS

This is a continuation-in-part of application Ser. No. 07/849,865, filed Mar. 12, 1992 now abandoned, which is a continuation-in-part of application Ser. No. 07/613,848, filed Dec. 6, 1990, abandoned, which is a continuation-in-part of application Ser. No. 07/204,659, filed Jun. 9, 1988, now abandoned, which is a continuation-in-part of application Ser. No. 07/144,602, filed Jan. 11, 1998, now U.S. Pat. No. 4,859,768, which is a continuation of application Ser. No. 06/629,660, filed Jul. 11, 1984, abandoned. The disclosures of application Ser. Nos. 07/613,848 and 07/849,865 and U.S. Pat. No. 4,859,768 are incorporated herein by reference.

REFERENCE TO GOVERNMENT GRANT

The invention described herein was made, in part, in the course of work supported by U.S. Public Health Services grant P30-CA12227 and National Science Foundation grant DMB-9004139. The government has certain rights in the invention.

FIELD OF THE INVENTION

The invention relates to synthetic analogues of naturally occurring antiviral 2',5'-oligoadenylates, pharmaceutical conjugates and compositions of such analogs, and the uses thereof. The compounds of this invention have antiviral activity and increased metabolic stability relative to their naturally occurring counter parts.

BACKGROUND OF THE INVENTION

The full nomenclature of the subject matter of the present invention involves lengthy terms. It is customary for those skilled in the art to abbreviate oligoadenylate analogues and related terms in a manner well known to the art. These general and customary abbreviations are set forth herein below and may be utilized in the text of this specification.

ABBREVIATIONS

A: adenosine or adenylate or adenylyl
2-5A: 2',5'- oligoadenylate or oligomer of adenylic acid with 2',5'-phosphodiester linkages and a 5'-terminal triphosphate group
ATP: adenosine triphosphate
C: cordycepin or 3'-deoxyadenosine or 3'-deoxyadenylyl
DBU: 1.8 diazabicyclo[5.3.0]undec-7-ene
DMAP: 4-(dimethylamino)pyridine
DMSO: dimethyl sulfoxide
DMT: dimethoxytrityl
dsRNA: double-stranded ribonucleic acid
EDC: N-(dimethylaminopropyl)-N'-ethylcarbodiimide hydrochloride
FABMS: fast atom bombardment mass spectroscopy
FC: flash chromatography
HIV: Human Immunodeficiency Virus, including HIV-1, HIV-2, and all other HIV subtypes
HTLV: Human T-cell Leukemia Virus, including HTLV-I, HTLV-II and HTLV-III, and all other HTLV subtypes
MeOTr: monomethoxytrityl
mRNA: messenger ribonucleic acid
npe: 2-(4-nitrophenyl)ethyl
npeoc: 2-(4-nitrophenyl)ethoxycarbonyl
PBL: peripheral blood lymphocytes
2'-PDE: 2'-phosphodiesterase
RNaseL: 2-5A-dependent endoribonuclease
rRNA: ribosomal ribonucleic acid
RT: reverse transcriptase
TBAF: tetrabutylammonium fluoride trihydrate
tbdmsCl: (tert-butyl)dimethylsilyl chloride
tbds: (tert-butyl)dimethylsilyl
THF: tetrahydrofuran 2-5A is a component of a natural, broad-spectrum antiviral defense mechanism in plants and animals. The 2-5A pathway, also known as the 2-5A/RNase L pathway or antiviral system, is generally regarded to be involved in the antiviral mechanism of interferon.

According to the pathway, 2-5A is synthesized from ATP by 2',5'-oligoadenylate synthetase (hereinafter "2-5A synthetase") and its only known chemical effect is the binding to and activation of RNase L. The latter cleaves viral and cellular mRNA or rRNA, thereby inhibiting protein synthesis. The activation of RNase L is transient unless 2-5A is continuously synthesized, since 2-5A is rapidly degraded. RNase L activation thus plays a critical role in inhibiting replication, and therefore in defending against infection by viruses.

A correlation has also been established between 2-5A metabolism and the growth cycle of HIV-1, i.e., high levels of 2-5A and activated RNase L correlate with the failure of infected cells to release HIV-1, Schroder et al, *J. Biol. Chem.* 264, 5669–5673 (1989). To activate RNase L, the naturally occurring 2-5A molecule requires a 5'-triphosphate, which is unstable. 2-5A molecules with 5'-monophosphates or no 5'-phosphate (core) do not activate RNase L at physiological concentrations.

The 2-5A synthetase/RNase L system as an antiviral cellular defense mechanism has been shown to be a promising target for antiviral chemotherapy, particularly due to its interaction with double-stranded segments within viral genomes or transcripts such as the HIV-1 RNA genome (Lengyel, *Annu. Rev. Biochem.* 51: 251 (1982); Pestka, ed., *Methods Enzymol.* 118, 119 (1986); Lengyel, *J. Interferon Res.* 7: 511 (1987); Sen, *Prog. Nucleic Acid Res. Molec. Biol.* 27: 105 (1982)). However, one of the main limitations in the application of synthetically modified 2',5'-oligoadenylates has been the low permeability of the polyanion species through the cell membrane. What is needed are derivatives of 2-5A which will override degradation by phosphodiesterase and phosphotase, enzymes which inactivate authentic 2-5A, and derivatives that can more effectively penetrate cellular membranes.

Compounds in which one or more of the 3'-hydroxyl groups have been replaced by hydrogen atoms to form the core 2',5'-cordycepin derivatives have resulted in derivatives with increased resistance to degradation by phosphodiesterase. The preparation of such compounds is disclosed in U.S. Pat. Nos. 4,464,359 (2',5'-oligocordycepin analogs) and 4,859,768 (2',5'-oligocordycepin and mixed 2',5'-oligocordycepin/adenosine analogs). Other 2-5A derivatives have been synthesized with other modifications of the 3'-hydroxyl groups, such as the substitution of amino and $OSi(CH_3)_2$-$C(CH_3)_3$, as described in U.S. Pat. No. 4,859,768. Other 2-5A derivatives contain, in addition to or in lieu of 3'-hydroxyl modifications on one or more nucleotides, modifications in the 5'-terminal phosphate group.

SUMMARY OF THE INVENTION

According to one embodiment, the invention comprises a novel compound of Formula I

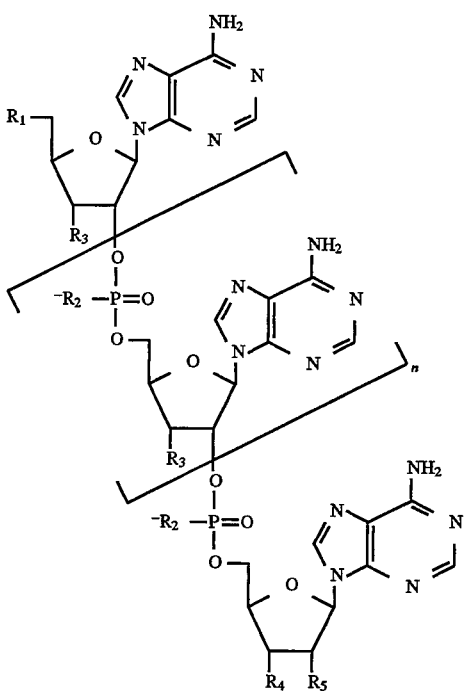

wherein:

n is an integer from 1 to 8;

$R_1$ is selected from the group of consisting of T, T' and Y, wherein

T is

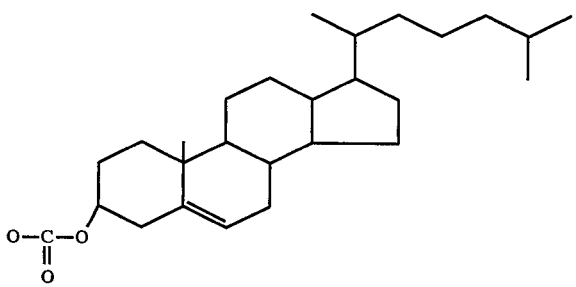

T' is

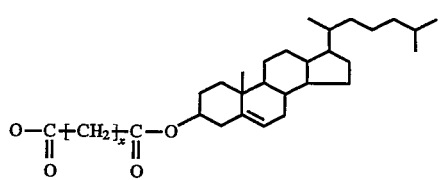

where x is an integer from 1 to 18;

Y is

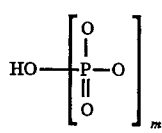

where m is zero, 1, 2, or 3;

each $R_2$ is independently selected from the group consisting of oxygen and sulfur;

each $R_3$ is independently selected from the group consisting of hydrogen and hydroxyl;

$R_4$ is selected from the group consisting of hydrogen, hydroxyl, T and T';

$R_5$ is selected from the group consisting of hydrogen, hydroxyl, T and T';

provided that all $R_1$, $R_4$ and $R_5$ may not be T or T';

at least one $R_3$ is hydrogen or $R_4$ is hydrogen; and at least one of $R_1$, $R_4$ and $R_5$ must be T or T';

or a water soluble salt thereof.

The invention also comprises a method of antiviral treatment by administering to a plant or mammal an effective amount of one or more compounds according to the above formula, or a water soluble salt thereof, and antiviral compositions containing such compounds with a carrier.

DETAILED DESCRIPTION OF THE INVENTION

Therapeutic agents that activate the 2-5A synthetase/RNase L antiviral defense pathway and that also inhibit the activity of virally-derived DNA polymers (particularly reverse transcriptase) may be used for the treatment of viruses, where the term "treatment" is also meant to include prophylaxis. Such dual effect therapeutic agents are selective, broad spectrum inhibitors of viral DNA polymerases that are produced during viral infection. The polymerases are critical for viral replication. The compounds utilized in the practice of the invention may be characterized as derivatives of authentic 2-5A with modifications in either the 2' or 5'-terminal moiety and/or the internucleotide linkage. These derivatives are metabolically more stable than authentic 2-5A, are non-toxic, and also inhibit retroviral reverse transcriptase. They are also characterized by enhanced cellular uptake.

The ability of the 2-5A conjugates to resist phosphodiesterase and phosphatases, and thus, their longer half-life, offers a more favorable therapeutic ratio. Compounds in which one or more cordycepin nucleotides are present in the oligonucleotide will have increased resistance to these enzymes. Additionally, it would appear that modification of the 5'-terminal nucleoside especially enhances the ability of the 2-5A molecule to activate RNase L. This allows a decreased frequency of administration relative to 2-5A, which is metabolically unstable. A decreased frequency of administration is important due to the chronic nature of retroviral diseases. In addition, conjugation with cholesterol facilitates penetration into the cell, further increasing the therapeutic ratio by reducing the amount of the derivative that must be administered to give a therapeutic effect.

Cholesterol conjugates according to the present invention have the potential to enter the cell by diffusion, owing to their lipophilic nature. They may be introduced into intact cells with increased biological activity relative to authentic 2-5A and without membrane damage. Once inside the cell, the conjugates are hydrolyzed and release the 2-5A derivative, although the 5'-cholesteryl conjugates may retain the cholesteryl moiety intact. Without wishing to be bound by any theory, the increased ability of the conjugates described herein to suppress reverse transcriptase replication is believed to be attributable to increased cellular uptake by either membrane fluidization or by receptor-mediated endocytosis.

This approach involves (i) the synthesis of bioactive, metabolically stable derivatives, e.g., 2',5'-oligocordycepin derivatives (prepared according to U.S. Pat. No. 4,464,359)

and other metabolically stable derivatives such as those disclosed in U.S. Pat. No. 4,859,768. Certain 2-5A derivatives according to the disclosure of the above-mentioned documents, have been designed, synthesized and tested for their antiretroviral effect at the level of RNase L and inhibition of RT, and are incorporated herein by reference. The 2-5A derivative conjugates according to the present invention are characterized by the attachment of a cholesterol moiety, through an appropriate chemical linker, to the 2'- or 5'-terminal nucleoside.

The 2-5A derivative conjugates of Formula I may be prepared by attaching the cholesterol via a carbonate (Formula T) or a diacid (Formula T') linker to a 2'- or a 5'-terminal nucleoside of a 2',5'-phosphodiester or a 2',5'-phosphorothioate oligonucleotide. The preparation of the 2',5'-phosphorothioates, including fully resolved enantiomers thereof, is disclosed in U.S. Pat. No. 4,924,624 and is incorporated herein by reference.

The substitution of sulfur for oxygen in the 2',5'-phosphodiester backbone referenced above, introduces chirality into the molecules and introduces a new chemistry of the backbone. The core 2',5'-phosphorothioates exhibit increased resistance to phosphodiesterase and phosphatases and new biological activities compared to authentic 2-5A cores. These stereochemically modified molecules act through both the activation of the 2-5A synthetase/RNase L antiviral system and the inhibition of viral DNA polymerase. The 2',5'-phosphorothioate trimer 5'-monophosphates activate RNase L at nanomolar concentrations, similar to naturally occurring 5'-triphosphate 2-5A.

The compounds of the present invention may be used as a treatment or prophylactically for humans and animals from viral infections such as Herpes simplex, rhinovirus, hepatitis and other infections of the hepatitis virus family, Epstein Barr virus, Chronic Fatigue Syndrome, measles virus, multiple sclerosis (which may be caused by a viral agent), and the various Human Immunodeficiency viruses ("HIV"), such as HIV-1, which causes cutaneous T-cell lymphoma; HIV-2, which causes Sezany lymphoma and HIV-3 which is responsible for causing acquired immune deficiency syndrome ("AIDS"). The compounds of the invention inhibit the HIV-1 induced syncytia formation. See Table 1, infra.

The synthesis described herein has been performed in solution using phosphoramidite chemistry. The synthesis begins with the esterification with cholesterol of a fully protected 2',5'-oligoadenylate monomer to form a monomer cholesterol-conjugate. Following selective deprotection of the monomer cholesterol-conjugate, the monomer is coupled with the phosphoramidite to form a protected dimer. The trimer analog with the cholesterol moiety in place is formed in a similar manner. The final deprotection of the blocking groups was done without purification of any intermediates to yield the cholesterol trimer conjugate.

While the preparation and examples that follow are directed to homopolymer cordycepin derivatives, the cholesterol conjugation described is equally applicable to the manufacture of oligomers comprising a mixture chain of cordycepin and adenosine residues as described in U.S. Pat. No. 4,859,768, or to compounds having phosphorothioate linkages in place of the phosphodiester linkages of authentic 2-5A. The preparation of 2-5A phosphorothioate analogs is disclosed in U.S. Pat. No. 4,924,624.

In a preferred embodiment of the invention n is preferably 1, 2 or 3, more preferably 1 or 2, and in the most perferred embodiment n is 1. In a preferred embodiment when $R_1$ or $R_5$ is T', x is preferably 1 to 7, more preferably 2–5, most preferably 2. Preferably, the oligomer includes at least one nucleotide residue which is cordycepyl, that is, at least one $R_3$ is hydrogen, or $R_4$ is hydrogen. Most preferably, the compounds of the present invention comprise cholesteryl conjugates of 2',5'-oligocordycepin, wherein the internucleotide linkages comprise phosphodiester groups, that is, all $R_2$ are oxygen and all $R_3$ and $R_4$ are hydrogen. The preparation of the compounds of the present invention is illustrated in more detail by reference to the following non-limiting examples.

Preparation of 2'-O-Cholesterylcarbonyl-Cordycepin Conjugate

The corresponding oligonucleotide conjugates have been achieved by stepwise syntheses (as shown in Schemes 1a and 1b) starting from the partially deprotected monomers 3 and 6, respectively. The partially deprotected monomers were condensed with 3'-deoxy-5'-O-monomethoxytrityl-6-N-[2-(4-nitrophenyl)ethoxycarbonyl]-adenosine 2'-[2-(4-nitrophenyl)ethyl-N,N-diisopropyl-phosphoramidite] 8 to give on subsequent oxidation of the intermediary phosphotriester the fully protected dimers 9 and 10. Detritylation of the dimers generated the 5'-OH building blocks 11 and 12 which, on further condensation with the phosphoramidite 8 and iodine oxidation, led to the cordycepin trimers 13 and 14. The final deprotection of the various blocking groups was achieved subsequently without purification of intermediates by DBU and acetic acid treatment to give the cordycepin trimer conjugates 15 and 16 as colorless powders.

Scheme 1a, which corresponds to Preparations 1 through 5, begins with the starting material 3'-deoxy-5'-O-monomethoxytrityl-6-N-[2-(4-nitrophenyl)-ethoxycarbonyl]-adenosine, 1. Reaction of 1 with cholesteryl chloroformate in anhydrous $CH_2Cl_2$ in the presence of N-methylimidazole and DMAP gave 2, which was subsequently detritylated to the intermediate 3. (See Preparation 1). The preparation for the remainder of Scheme 1a continues with Preparation 2 and concludes with the formation of the monomer cordycepin conjugate outlined in Preparation 5.

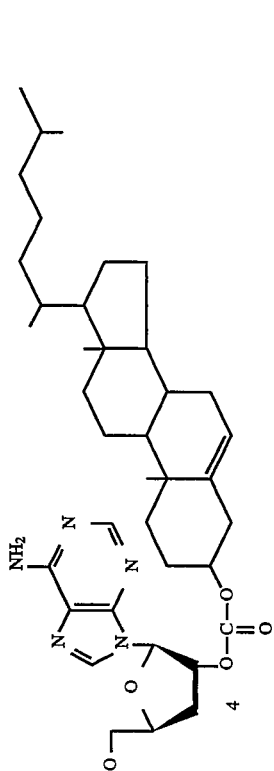
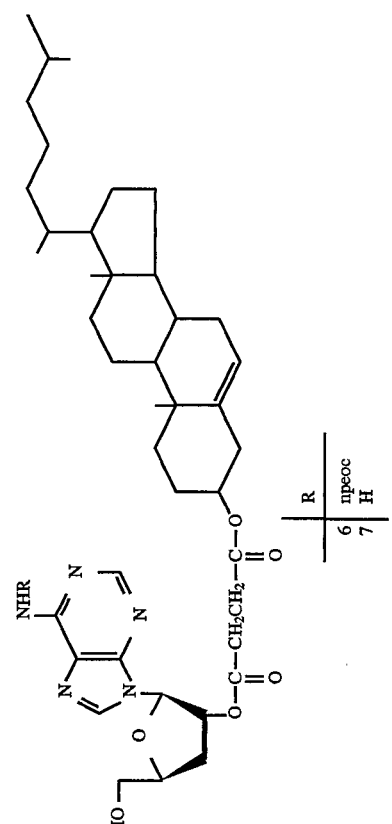
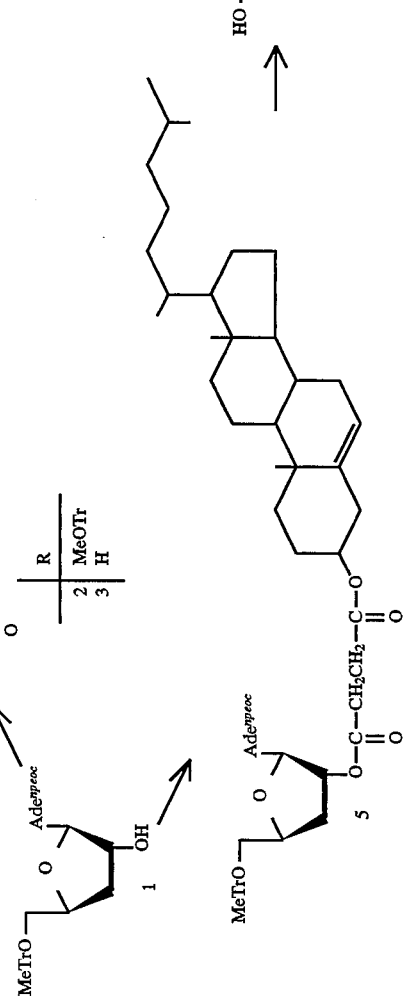
npeoc = 2-(4-nitrophenyl)ethoxycarbonyl
tbds = (tert-butyl)dimethylsilyl
MeOTr = monomethoxytrityl
npe = 2-(4-nitrophenyl)ethyl

MATERIALS AND METHODS

Precoated silica gel sheets F 1500 LS 254 and silica gel plates 60 $PF_{254}$ used for analytical thin layer chromatography (TLC) were obtained from Schleicher & Schüll and Merck, respectively. The silica gel used for prep. column flash-chromatography (FC) was obtained from Baker.

Analytical high performance liquid chromatography (HPLC) was performed on a Merck-Hitachi L-6200, L-3000 Photo Diode Array detector, column RP 18, 125×4 mm, 5 µm, Merck, flow rate 1 ml/min, mobile phase: A:O. 1M TEAAc buffer pH 7/$CH_3CN$; gradient: 0 min: 100% A; 5 min: 100% A; 35 min: 100% B; 40 min: 100% B. The separated compounds were detected by absorption of ultraviolet/visible (UV/VIS) light from a Perkin Elmer, Lambda 5; $\lambda_{max}$ in nm (log ε). All $^1H$ nuclear magnetic resonance (NMR) were recorded on a Bruker AC 250 spectrometer using δ in ppm to DMSO, Californium-252. Plasma desorption mass spectrometry was recorded on a Bioion 20 PDMS from Bio-Ion Nordic (Uppsala, Sweden). Fast atom bombardment mass spectroscopy was conducted on a Finnigan MAT 312/AMD-5000 mass spectrometer.

Sup T1 cells were obtained from the AIDS Research and Reference Reagent Program and were maintained in RPMI-1640 medium supplemented with 10% fetal calf serum as described in Henderson et al., *Virology*, 182: 186–198 (1994).

Preparation 1

2'-O-Cholesteryloxycarbonyl-3'-deoxy-6-N-[2-(4-nitrophenyl)ethoxycarbonyl]-adenosine 3

To an ice-cooled solution of 1 g (1.4 mmol) 3'-deoxy-5'-O-monomethoxytrityl-6-N-[2-(4-nitrophenyl)-ethoxycarbonyl]-adenosine 1 in 10 ml absolute ("abs.") $CH_2Cl_2$ prepared according to the method of Charubala et al., *Helv. Chim. Acta* 70: 2028–2038 (1987), 286 mg (3.5 mmol) of N-methylimidazole and catalytic amounts of DMAP was added. A solution of 1.57 g (3.5 mmol) cholesteryl chloroformate in 15 ml absolute $CH_2Cl_2$ was added dropwise. The reaction was kept at room temperature ("r.t.") for 32 h, evaporated to dryness, diluted with 250 ml of EtOAc, extracted with a saturated, aqueous solution of NaCl (3×60 ml) and back-extracted with EtOAc. The organic layer was dried ($MgSO_4$) and evaporated to give 2'-O-cholesteryloxycarbonyl-3'-deoxy-5'-O-monomethoxytrityl-6-N-[2-(4-nitrophenyl)ethoxycarbonyl]-adenosine 2, which was detritylated without further purification. In the detritylation procedure the residue (2.20 g) was dissolved in 30 ml of $CH_2Cl_2$/MeOH 4:1 containing 2% of TsOH. $H_2O$ and kept at r.t. for 20 minutes. The resulting mixture was diluted with $CHCl_3$ (150 ml), washed with saturated $NaHCO_3$ solution (2×120 ml) and again back-extracted. The organic layer was dried ($MgSO_4$), evaporated and the residue purified by flash chromatography ("FC") (silica gel, 18×3 cm, gradient toluene/EtOAc 1:1 to toluene/EtOAc 1:1+2% MeOH) to yield 923 mg (77%) of the partially deblocked intermediate 3 as an amorphous solid. UV (MeOH): 298 (sh, 4.38), 267 (4.41). $^1$H-NMR (($D_6$)DMSO): 10.61 (s,NH); 8.65, 8.61 (2s, H—C(8), H—C(2)); 8.15 (d,2H o to $NO_2$); 7.60 (d,2H m to $NO_2$); 6.23 (s,H—C(1')); 5.59 (m,H—C(2')); 5.31 (m, olef. H at chol.); 5.07 (t, OH—C(5')); 4.38 (m,H—C(4'), $OCH_2CH_2$(6-N), H—C(3) at chol.); 3.68 (m,H—C(5')); 3.10 (t, $OCH_2CH_2$); 2.58–0.62 (m, 45H, 2×H—C (3'), chol.). Anal. calc. for $C_{47}H_{64}N_6O_9$×$H_2O$ (875.1):C 64.51, H 7.60, N 9.60; found: C 64.84, H 7.68, N 9.51.

Preparation 2

2'-O-Cholesteryloxycarbonyl-3'-deoxyadenosine 4

This preparation outlines the procedure for the cleavage of the npeoc blocking group using DBU in a β elimination process to give the monomer conjugate with a carbonyl linkage. Accordingly, to 200 mg (0.23 mmol) of the partially deblocked monomer 3 0.5M DBU in dry pyridine (9.2 ml) was added. The mixture was stirred at r.t. for 20 h, neutralized with 1M AcOH in pyridine (4.6 ml) and evaporated. The residue was diluted with $CHCl_3$(50 ml), extracted with water (3×30 ml) and back-extracted. The organic layer was dried ($MgSO_4$), evaporated and coevaporated with toluene. The residue was treated with 10 ml of hot MeOH. After filtration 95 mg (61%) of the monomer conjugate 4was obtained as a solid. Another 20 mg of product (13%) was isolated from the mother liquor. UV (MeOH): 259 (4.15). $^1$H-NMR ($CDCl_3$): 8.33, 7.87 (2s, H—C(8), H—C(2)); 5.98 (m, H—C(1'), OH—C(5')); 5.75 (b, $NH_2$); 5.57 (m, H—C (2')); 5.38 (m, olef. H at chol.); 4.59 (t, H—C(5')); 4.44 (m, H—C(3) at chol.); 4.10 (m, H—C(4')); 3.65 (t, H—C(5')); 2.99 (m, H—C (3')); 2.37–0.67 (m, 44H, H—C (3'), chol.). Anal. calc. for $C_{38}H_{57}N_5O_5$(663.9): C 68.75, H 8.65, N 10.55; found: C 68.24, H 8.62, N 10.59.

Preparation 3

2'-O-[2-(Cholesteryloxycarbonyl)ethylcarbonyl]-3'-deoxy-5'-O-monomethoxytrityl-6-N-[2-(4-nitrophenyl)ethoxycarbonyl]-adenosine 5

Compound 5 was prepared in a one-pot reaction where a mixture of 1 g (1.4 mmol) 1, 168 mg (1.68 mmol) of succinic acid anhydride, and 222 mg (1.82 mmol) of DMAP in absolute $CH_2Cl_2$ (7 ml) was kept at r.t. for 2.5 h. Esterification with cholesterol was accomplished by adding 349 mg (1.82 mmol) of EDC, 758 mg (1.96 mmol) of cholesterol, and catalytic amounts of DMAP to the mixture. The reaction was kept at r.t. for 1.5 h, diluted with $CHCl_3$ (100 ml), washed with saturated $NaHCO_3$ solution (2×50 ml) and back-extracted. The organic layer was dried ($MgSO_4$) and evaporated. The crude product was purified by FC (silica gel, 14×3 cm, gradient toluene to toluene/EtOAc 1:1) to give 1.11 g 867%) of the monomer conjugate 5 with a succinyl linkage as an amorphous solid. UV (MeOH): 298 (sh, 3.57), 272 (sh, 4.41), 267 (4.44), 235 (4.30). $^1$H-NMR ($CDCl_3$): 8.69, 8.21–8.12 (3s, d, H—C(2), NH, 2H o to $NO_2$)); 7.46–7.20 (m, 14H, 2H m to $NO_2$, MeOTr); 6.80 (d, 2H o to MeO); 6.15 (s, H—C(1')); 5.77 (d, H—C (2')); 5.35 (m, olef. H at chol.); 4.62–4.51 (m, H—C(4'), H—C(3) at chol.); 4.53 (t, $OCH_2CH_2$ (6-N)); 3.78 (s, MeO); 3.41–3.37 (m, 2×H—C(5')); 3.16 (t, $OCH_2CH_2$(6-N)); 2.69–2.64 (m, $CH_2CH_2$ (succ.), H—C (3')); 2.32–0.67 (m, 44H, H—C(3'), chol.). Anal. calc. for $C_{70}H_{84}N_6O_{11}$×$H_2O$ (1203.6): C 69.68, H 7.20, N 6.98; found: C 69.92, H 7.23, N 6.67.

Preparation 4

2'-O-[2-(Cholesteryloxycarbonyl)ethylcarbonyl]-3'-deoxy-6-N-[2-(4-nitrophenyl)-ethoxycarbonyl]-adenosine6

A mixture of 1.19 g (1 mmol) of the fully protected monomer 5 was stirred at r.t. in 20 ml of $CH_2Cl_2$/MeOH 4:1 containing 2% of TsOH ×$H_2O$ for 15 minutes. The mixture was then diluted with $CHCl_3$ (130 ml), washed with saturated $NaHCO_3$ solution (3×50 ml) and back-extracted. The organic layer was dried ($MgSO_4$) and evaporated. The residue was purified by FC (silica gel, 14×3 cm, gradient toluene to toluene/EtOAc 3:2 to toluene/EtOAc 1:1+5% MeOH) to give 886 mg (97%) of the partially deprotected monomer with a succinyl linkage 6 as an amorphous solid. UV (MeOH): 296 (sh, 3.64), 272 (sh, 4.40), 267 (4.44). $^1$H-NMR (CDCl$_3$): 8.71, 8.08 (2s, H—C(8), H—C(2)); 8.44 (b, NH); 8.17 (d, 2H o to NO$_2$); 7.44 (d, 2H, m to NO$_2$); 6.00 (d, H—C(1')); 5.53 (m, H—C (2')); 5.36 (m, olef. H at chol.); 4.55 (m, H—C (4'), OCH$_2$CH$_2$(6-N), H—C(3) at chol.); 4.10 (m, H—C(5')); 3.68 (m, H—C(5')); 3.15 (t,OCH$_2$CH$_2$(6-N)); 2.89 (m, H—C(3')); 2.63 (s, CH$_2$CH$_2$ (succ.)); 2.32–0.68 (m, 44H, H—C (3'), chol.). Anal. calc. for C$_{50}$H$_{68}$N$_6$O$_{10}$×H$_2$O (931.2); C 65.12, H 7.54, N 9.11; found: C 64.86, H 7.62, N 9.12.

Preparation 5

2'-O-[2-(Cholesteryloxycarbonyl)ethylcarbonyl]-3'-deoxyadenosine 7

Preparation 5 is analogous to Preparation 2 for the cleavage of the npeoc protecting group by β-elimination to give the monomer conjugate with a succinyl linkage. To 183 mg (0.2 mmol) of the partially deprotected monomer 6, which was coevaporated twice in absolute pyridine, was added 0.5M DBU in dry pyridine (7.9 ml). The mixture was stirred at r.t. for 18 h, neutralized with 1M AcOH in pyridine (3.85 ml) and evaporated. The residue was diluted with CHCl$_3$ (60 ml), extracted with water (3×25 ml) and back-extracted. The organic layer was dried (MgSO$_4$), evaporated and coevaporated with toluene. The residue was crystallized in 15 ml EtOH to give 72 mg (50%) of the monomer conjugate 7 as colorless crystals (m.p.: 208° C.). Another 10 mg of product (7%) was isolated from the mother liquor. UV (MeOH): 259 (4.15). $^1$H-NMR ((D$_6$)DMSO): 8.32, 8.11 (2s, H—C(8), H—C(2)); 7.31 (s, NH$_2$); 6.06 (d, H—C(1')); 5.60 (d, H—C(2')); 5.30 (m, olef. at chol.); 5.13 (t, OH—C(5')); 4.43 (m, H—C(3) at chol.); 4.24 (m, H—C(4')); 3.63 (m, H—C (5')); 2.55 (m, 5H, H—C (3'), CH$_2$CH$_2$ (succ.)); 2.24–0.63 (m, 44H, H—C (3'), chol.). Anal. calc. for C$_{41}$H$_{61}$N$_5$O$_6$× H$_2$O) (738.0): C 67.50, H 8.57, N 9.61; found: C 67.60, H 8.55, N 9.41.

Preparation 6 begins the reaction scheme shown in Scheme 1b. The starting material, 1, is reacted to form the phosphoramidite, 8, which is the primary reagent for the synthesis of the fully protected dimer with a carbonyl linkage, 9, and its structural analog utilizing a succinyl linkage, 10. The scheme is continued with the formation of the fully protected trimer conjugates, 13 and 14 respectively. The deblocked trimer carbonyl conjugates, 15 and 16 complete the reaction scheme and are prepared as set forth in Examples 1 and 2.

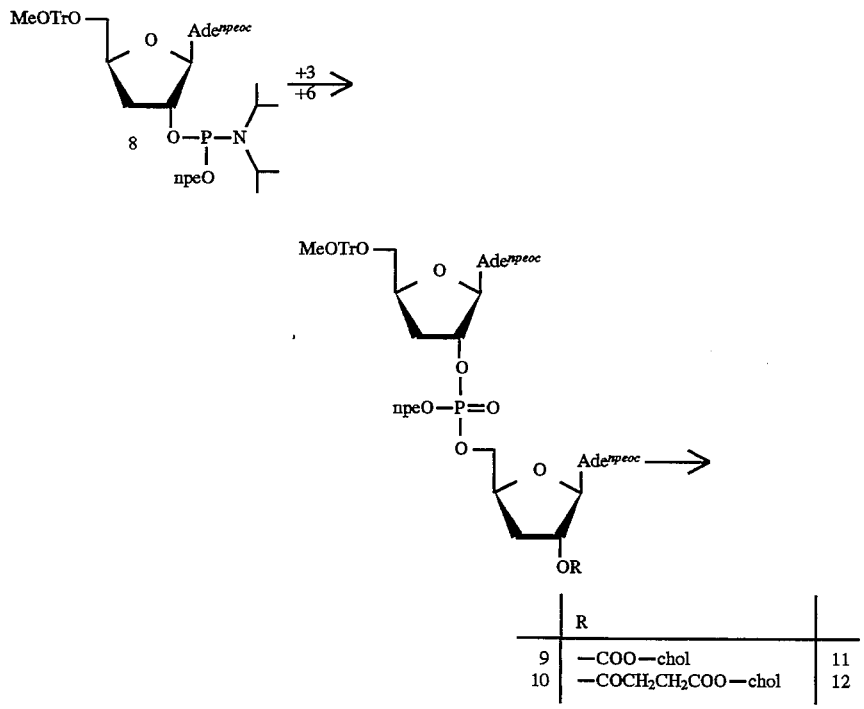

|    | R              |    |
|----|----------------|----|
| 9  | —COO—chol      | 11 |
| 10 | —COCH$_2$CH$_2$COO—chol | 12 |

-continued
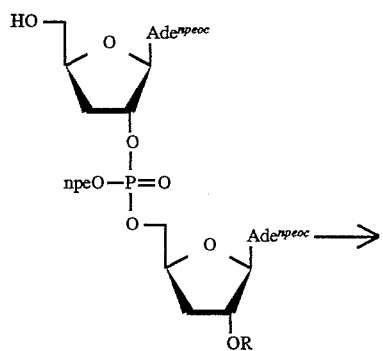
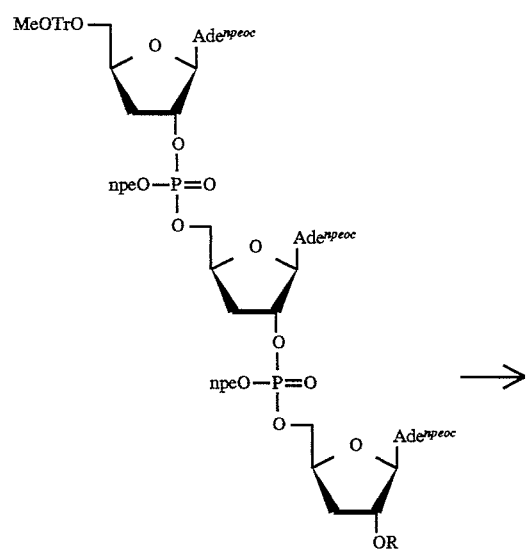
| | R |
|---|---|
| 13 | —COO—chol |
| 14 | —COCH₂CH₂COO—chol |

-continued

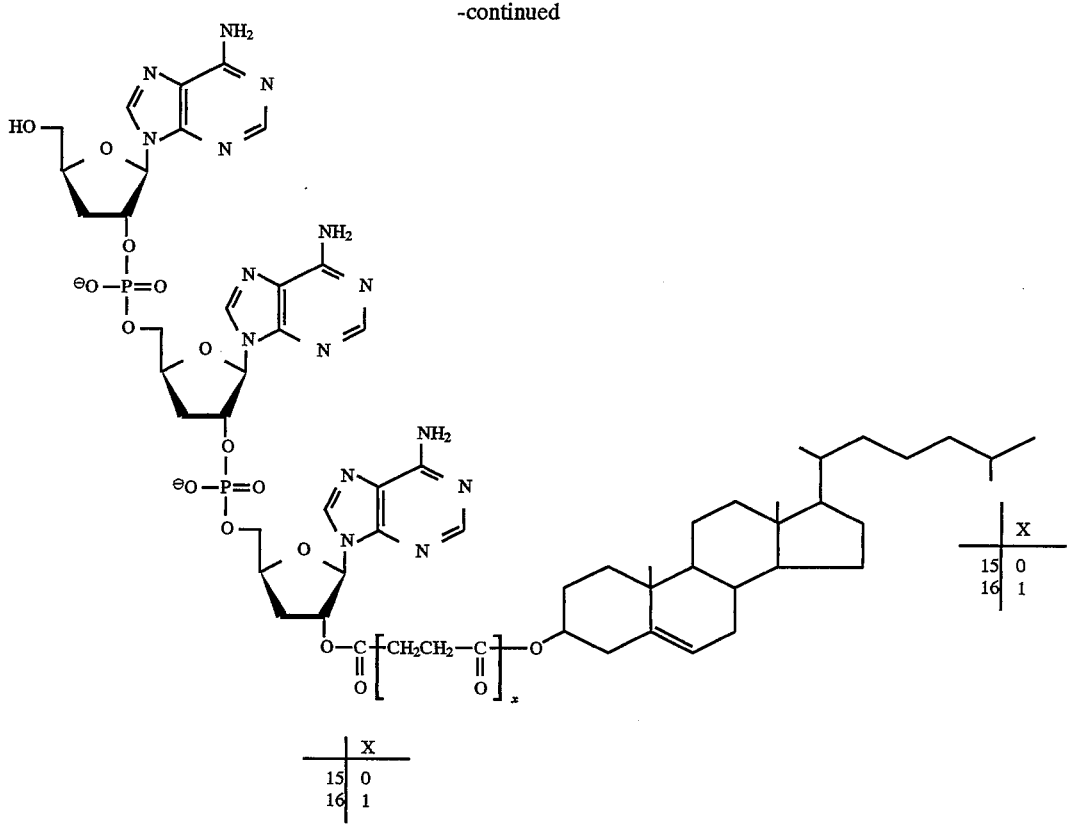

| x | |
|---|---|
| 15 | 0 |
| 16 | 1 |

| x | |
|---|---|
| 15 | 0 |
| 16 | 1 |

Preparation 6

3'-Deoxy-5'-O-monomethoxytrityl-6-N-[2-(4-nitrophenyl)ethoxycarbonyl]-adenosine-2'-[2-(4-nitrophenyl)ethyl-N,N-diisopropyl-phosphoramidite] 8

The preparation of the phosphoramidite, prepared according to the method of Schirmeister et al., Helv. Chim. Acta, 77: 10– (1994), begins with a mixture of 1.8 g (2 mmol) of 3'-deoxy-5'-O-monomethoxytrityl-6-N-[2-(4-nitrophenyl) ethoxycarbonyl]-adenosine 1, 1.59 g (4 mmol) of bis (diisopropylamino)-2-(4-nitrophenyl) ethoxyphosphane, and 70 mg (1 mmol) of tetrazole in 10 ml anhydrous $CH_3CN$ kept at r.t. for 2 h. The mixture was then diluted with $CHCl_3$ (100 ml) and extracted with a solution of $NaCl/NaHCO_3$ 4:1 and back-extracted. The organic layer was dried ($MgSO_4$) and evaporated. The residue was purified by FC (silica gel, 15×2 cm, toluene/EtOAc 1:1) to give 1.82 g (90%) of the phosphoramidite 8 as an amorphous solid. UV (MeOH): 268 (4.56), 233 (4.35). $^1$H-NMR ($CDCl_3$): 8.69, 8.21–8.00 (s, m, NH, H—C(8), H—C(2), 4H o to $NO_2$); 7.47–7.16 (m, 4H m to $NO_2$, 12H MeOTr); 6.82 (2d, 2H o to MeO); 6.15 (s, H—C(1')); 4.92 (m, H—C(2')); 4.62 (m, H—C(4')); 4.53 (m, $OCH_2CH_2$); 3.96–3.81 (m, $OCH_2CH_2$); 3.79 (2s, MeO); 3.55 (m 2×CH (isopropylamide)); 3.43 (m, H—C(5'); 3.35 (m, H—C(5')); 3.16 (2t, $OCH_2CH_2$); 2.97 (m, $OCH_2CH_2$); 2.29 (m, H—C (3')); 2.10 (m, H—C (3')); 1.11 (m, 4×$CH_3$). $^{31}$P-NMR ($CDCl_3$): 149.54; 148.62. Anal. calc. for $C_{53}H_{57}N_8O_{11}P$ (1013.1): C 62.84, H 5.67, N 11.06; found: C 62.60, H 5.82, N 10.82.

Preparation 7

3'-Deoxy-5'-O-monomethoxytrityl-6-N-[2-(4-nitrophenyl)ethoxycarbonyl]-adenylyl-[2'-[$O^P$-(2-(4-nitrophenyl)ethyl)]→5']-2'-O-cholesteryloxycarbonyl-3'-deoxy-6-N-[2-(4-nitrophenyl)ethoxycarbonyl]-adenosine 9

To prepare the fully protected dimer, a mixture of 470 mg (0.55 mmol) of 2'-O-cholesteryloxycarbonyl-3'-deoxy-6-N-[2-(4-nitrophenyl)ethoxycarbonyl]-adenosine 3, 1.11 g (1.1 mmol) of phosphoramidite 8, and 191 mg (2.74 mmol) of tetrazole was stirred in dry $CH_3CN$ (4 ml) and dry $CH_2Cl_2$ (1 ml) under nitrogen at r.t. for 2 h. The mixture was then oxidized with a solution of $I_2$ (500 mg) in pyridine (3 ml), $CH_2Cl_2$ (1 ml) and $H_2O$ (1 ml) until no change of color was detected. The mixture was stirred for 15 minutes and then diluted with $CHCl_3$ (100 ml), washed with a solution of $Na_2S_2O_3/NaCl$ (2×50 ml) and back-extracted. The organic layer was dried ($MgSO_4$), evaporated and coevaporated with toluene. The residue was purified by FC (silica gel, 16×3 cm, gradient toluene/AcOEt 1:1+4% MeOH to toluene/EtOAc 1:1+5% MeOH) to give 863 mg (88%) of the fully protected dimer with a carbonyl linkage as an amorphous solid. UV (MeOH): 296 (sh, 4.11), 274 (sh, 4.73), 267 (4.79), 237 (sh, 4.47). $^1$H-NMR ($CDCl_3$): 8.70–8.00 (m, 2×NH, 2×H—C(8), 2×H—C(2), 3×2H o to $NO_2$); 7.45–7.10 (m, 3×2H m to $NO_2$, 12H, MeOTr); 6.79 (d, 2H o to MeO); 6.19–6.10 (m, H—C(1')); 5.64 (m, H—C(2')); 5.40 (m, H—C(2'), olef. H at chol.); 4.60–4.20 (m, 2×H—C(4'), H—C(3) at chol., 3×$OCH_2CH_2$, 2×H—C(5')); 3.77 (s, MeO), 3.40 (m, 2×H—C(5')); 3.22–0.67 (m, 3×$OCH_2CH_2$, 4×H—C(3'), 43H chol.). Anal. calc. for $C_{94}H_{106}N_{13}O_{21}P$ ×$H_2O$ (1802.9): C 62.62, H 6.04, N 10.10; found: C 62.44, H 6.03, N 9.67.

Preparation 8

3'-Deoxy-5'-O-monomethoxytrityl-6-N-[2-(4-nitrophenyl)ethoxycarbonyl]-adenylyl-{2'-[O$^P$-(2-(4-nitrophenyl)ethyl)]→5'}-2'-O-[2-(cholesteryloxycarbonyl)ethylcarbonyl]-3'-deoxy-6-N-[2-(4-nitrophenyl)ethoxycarbonyl]-adenosine 10

Analogous to the preparation of the fully protected dimer with the carbonyl linkage, the fully protected dimer with a succinyl linkage is prepared by a mixture of 456 mg (0.5 mmol) of 2'-O-[2-(cholesteryloxycarbonyl)ethylcarbonyl]-3'-deoxy-6-N-[2-(4-nitrophenyl)ethoxycarbonyl]-adenosine 6, 709 mg (0.7 mmol) of phosphoramidite 8 and 140 mg (2 mmol) of tetrazole stirred in anhydrous $CH_2Cl_2$ (2.5 ml) under nitrogen at r.t. for 1 h. Another 305 mg (0.3 mmol) of 6 was added to the reaction and kept at r.t. for 4 h. The mixture was then oxidized with a solution of $I_2$ (500 mg $I_2$, 3 ml pyridine, 1 ml $CH_2Cl_2$, 1 ml $H_2O$) until no change of color was detected. The mixture was stirred for 15 minutes and then diluted with $CHCl_3$ (80 ml), washed with a solution of $Na_2S_2O_3$/NaCl (2×30 ml) and back-extracted. The organic layer was dried ($MgSO_4$), evaporated and coevaporated with toluene. The residue was purified by FC (silica gel, 17×3 cm, toluene/EtOAc 1:1+6% MeOH) to give 840 mg (91%) of the fully protected dimer with a succinyl linkage as an amorphous solid. UV (MeOH): 296 (sh, 4.13), 272 (sh, 4.73), 267 (4.76), 238 (sh, 4.45). $^1$H-NMR ($CDCl_3$): 8.70–8.62, 8.20–8.06 (4s, 2×NH, 2×H—C(8), 2×H—C(2), 3×2H o to $NO_2$); 7.47–7.19 (m, 3×2H m to $NO_2$, 12H MeOTr); 6.80 (d, 2H o to MeO), 6.20 (d, H—C(1')); 6.05 (s, H—C(1')); 5.60 (m, H—C(2')); 5.45 (m, H—C(2')); 5.35 (m, olef. H at chol.)); 4.65–4.50 (m, 2×H—C(4'), H—C(3) at chol., 2×OCH$_2$CH$_2$); 4.45–4.22 (m, OCH$_2$CH$_2$, 2×H—C(5')); 3.78 (s, MeO), 3.42–3.30 (m, 2×H—C(5'); 3.20–3.00 (m, 3×OCH$_2$CH$_2$); 2.67–0.67 (m, $CH_2CH_2$ (succ.), 4×H—C(3'), 43H chol.). Anal. calc. for $C_{97}H_{110}N_{13}O_{22}P$ ×$H_2O$ (1859.1): C 62.67, H 6.07, N 9.79; found: C 62.42, H 6.03, N 9.63.

Preparation 9 a. 3'-Deoxy-6-N-[2-(4-nitrophenyl)ethoxycarbonyl]-adenylyl-{2'-[O$^P$-(2-(4-nitrophenyl)ethyl)]→5'}-2'-O-cholesteryloxycarbonyl-3'-deoxy-6-N-[2-(4-nitrophenyl)ethoxycarbonyl]-adenosine 11 b. 3'-Deoxy-6-N-[2-(4-nitrophenyl)-ethoxycarbonyl]-adenylyl-{2'-[O$^P$-(2-(4-nitrophenyl)-ethyl)]→5'}-2'-O-(2-cholesteryloxycarbonylethylcarbonyl)-3'-deoxy-6-N-[2-(4-nitrophenyl)-ethoxycarbonyl]-adenosine 12

The preparation of the titled compounds 11 and 12 was analogous through the purification phase, wherein either 863 mg (0.48 mmol) of 9 or 565 mg (0.3 mmol) of 10 was stirred in $CH_2Cl_2$/MeOH 4:1 (9.7/16 ml) containing 2% of TsOH ×$H_2O$ for 1 h at r.t. The mixture was then diluted with $CHCl_3$ (120/180 ml), washed with a saturated $NaHCO_3$ solution (2×50/2×30 ml) and back-extracted. The organic layer was dried ($MgSO_4$) and evaporated. The residue for 11 was purified by FC (silica gel, 16.5×3 cm, gradient toluene/AcOEt 1:1+4% MeOH to toluene/EtOAc 1:1+15% MeOH) to give 600 mg (82%) of the 5'-OH intermediate with a carbonyl/succinyl linkage as an amorphous solid. UV (MeOH): 296 (sh, 4.07), 274 (sh, 4.71), 267 (4.76). $^1$H-NMR (($D_6$)DMSO): 10.61 (b, 2×NH); 8.63–8.53 (m, 2×H—C(8), 2×H—C(2)); 8.16–8.02 (m, 3×2H o to $NO_2$); 7.62–7.37 (m, 3×2H m to $NO_2$); 6.23–6.15 (m, 2×H—C(1')); 5.62 (m, H—C(2')); 5.31 (m, olef. H at chol.)); 5.26 (m, H—C(2')); 5.11 (m, OH—C(5')); 4.50–4.10 (m, 2×H—C (4'), H—C(3) at chol., 3×OCH$_2$CH$_2$, 2×H—C(5')); 3.45 (m, H—C(5')); 3.10 (m, 2×OCH$_2$CH$_2$); 2.93 (m, OCH$_2$CH$_2$); 2.65–0.62 (m, 4×H—C(3'), 43H chol.). Anal. calc. for $C_{74}H_{90}N_{13}O_{20}P$ (1512.6): C 58.76, H 6.00, N 12.04; found: C 58.58, H 6.05, N 12.02.

The residue for 12 was purified by FC (silica gel, 11×3 cm, gradient toluene/EtOAc 1:1+4% MeOH to toluene/EtOAc 1:1+12% MeOh) to give 437 mg (91%) of the 5'-OH intermediate with a succinyl linkage an amorphous solid. UV ($CH_2Cl_2$): 298 (sh, 4.74), 272 (sh, 4.17), 267 (4.78). $^1$H-NMR (($D_6$)DMSO): 10.5(b, 2×NH); 8.62–8.54 (m, 2×H—C(8), 2×H—C(2)); 8.33–8.02 (m, 3×2H o to $NO_2$); 7.61–7.37 (m, 3×2H m to $NO_2$); 6.19–6.14 (m, 2×H—C(1')); 5.70 (m, H—C(2')); 5.23 (m, H—C(2'), olef. H at chol.); 5.10 (t, OH—C(5')); 4.45–4.15 (m, 2×H—C(4'), H—C (3) at chol., 3×OCH$_2$CH$_2$, 2×H—C(5')); 3.69 (m, H—C(5')); 3.50 (m, H—C(5')); 3.10 (m, 2×OCH$_2$CH$_2$); 2.92 (t, OCH$_2$CH$_2$); 2.55 (m, $CH_2CH_2$ (succ.)); 2.48–0.60 (m, 4×H—CC(3'), 43H chol.). Anal. calc. for $C_{77}H_{94}N_{13}O_{21}P$ (1568.7): C 58.96, 6.04, N 11.61; found: C 58.64, H 6.00, N 11.64.

Preparation 10 a. 3'-Deoxy-5'-O-monomethoxytrityl-6-N-[2-(4-nitrophenyl)ethoxycarbonyl]-adenylyl-{2'-[O$^P$-(2-(4-nitrophenyl)ethyl)]→5'}-3'-deoxy-6-N-[2-(4-nitrophenyl)ethoxycarbonyl]-adenylyl-{2'-[O$^P$-(2-(4-nitrophenyl)ethyl)]→5'}-2'-O-cholesteryloxycarbonyl-3'-deoxy-6-N-[2-(4-nitrophenyl)ethoxycarbonyl]-adenosine 13 b. 3'-Deoxy-5'-O-monomethoxytrityl-6-N-[2-(4-nitrophenyl)ethoxycarbonyl]-adenylyl-{2'-[O$^P$-(2-(4-nitrophenyl)ethyl)]→5'}-3'-deoxy-6-N-[2-(4-nitrophenyl)ethoxycarbonyl]-adenylyl-{2'-[O$^P$-(2-(4-nitrophenyl)ethyl)]→5'}-2'-O-[2-(cholesteryloxycarbonyl)ethylcarbonyl]-3'-deoxy-6-N-[2-(4-nitrophenyl)ethoxycarbonyl]-adenosine 14

The preparation of the titled compounds, 13 and 14 was analogous through the purification phase, wherein either 600 mg (0.4 mmol) of 11 or 157 mg (0.1 mmol) of 12 and 800/204 mg (0.79/0.4 mmol) of phosphoramidite 8 and 140/35 mg (2/0.5 mmol) of tetrazole were stirred in anhydrous $CH_3CN$ (3/1 ml) and anhydrous $CH_2Cl_2$(1/0.15 ml) under nitrogen at r.t. for 2 h. The mixture was then oxidized with a solution of $I_2$ (500 mg $I_2$, 3 ml pyridine, 1 ml $CH_2Cl_2$, 1 ml $H_2O$) until no color change was detected. The mixture was stirred for 15 minutes and then diluted with $CHCl_3$ (100/40 ml), washed with a solution of $Na_2S_2O_3$/NaCl (2×40 ml ) and back-extracted. The organic layer was dried ($MgSO_4$), evaporated and coevaporated with toluene. The residue for the fully protected carbonyl trimer 13 was purified by FC (silica gel, 14×3 cm, gradient $CHCl_3$+1% MeOH to $CHCl_3$+5% MeOH) to give 748 mg (78%) of 13 and 208 mg (21%) of an impure fraction as an amorphous solid. UV (MeOH): 272 (sh, 4.90), 267 (4.93), 238 (sh, 4.55). $^1$H-NMR ($CDCl_3$): 9.62–7.85 (m, 3×NH, 3×H—C(8), 3×H—C(2), 5×2H o to $NO_2$); 7.45–7.12 (m, 5×2H m to $NO_2$, 12H MeOTr); 6.79 (d, 2H, o to MeO); 6.15 (m, 2×H—C(1')); 6.00 (d, H—C(1')); 5.68 (m, H—C(2')); 5.60–5.20 (m, 2×H—C (2'), olef. H at chol.); 4.60–4.12 (m, 3×H—C(4'), H—C(3) at chol., 5×OCH$_2$CH$_2$, 4×H—C(5')); 3.77 (s, MeO); 3.42 (dd, H—C(5')); 3.37 (dd, H—C(5')); 3.20–3.00 (m, 5×OCH$_2$CH$_2$); 2.75 (m, H—C (3')); 2.55 (m, H—C(3')); 2.50–0.68 (m, 4×H—C(3'), 43H chol.). Anal.

calc. for $C_{121}H_{132}N_{20}O_{32}P_2 \times H_2O$ (2440.4): C 59.55, H 5.45, N 11.48; found: C 59.03, H 5.36, N 11.39.

The residue for the fully protected succinyl trimer 14 was purified by FC (silica gel, 13×2 cm, gradient $CHCl_3$+1% MeOH to $CHCl_3$+3% MeOH) to give 234 mg (94%) of an amorphous solid. UV (MeOH): 296 (sh, 4.93), 274 (sh, 4.87), 267 (4.93), 235 (sh, 4.53). $^1$H-NMR ($CDCl_3$): 8.69–8.51, 8.26–8.03 (m, 3×NH, 3×H—C(8), 3×H—C(2), 5×2H o to $NO_2$); 7.46–7.16 (m, 5×2H m to $NO_2$, 12H MeOTr); 6.79 (d, 2H o to MeO); 6.18 (d, H—C(1')); 6.08 (d, H—C(1')); 5.99 (d, H—C(1')); 5.75 (m, H—C(2')); 5.60–5.30 (m, 2×H—C(2'), olef. H at chol.); 4.65–4.20 (m, 3×H—C(4'), H—C(3) at chol., 5×$OCH_2CH_2$, 4×H—C(5')); 3.77 (s, MeO); 3.47 (m, H—C(5')); 3.35 (m, H—C(5')); 3.20–3.00 (m, 5×$OCH_2CH_2$); 2.47 (b, $CH_2CH_2$ (succ.)); 2.35–0.67 (m, 6×H—C(3'), 43H chol.). Anal. calc. for $C_{124}H_{136}N_{20}O_{33}P_2$ (2496.6): C 59.66, H 5.49, N 11.22; found: C 59.75, H 5.52, N 11.00.

EXAMPLE 1 a. 3'-Deoxyadenylyl-(2'→5')-3'-deoxyadenylyl-(2'→5')-2'-O-cholesteryl-carbonyl-3'-deoxyadenosine 15 b. 3'-Deoxyadenylyl-(2'→5')-3'-deoxyadenylyl-(2'→5')-2'-O[2(cholesteryloxycarbonyl)ethylcarbonyl]-3'-deoxyadenosine 16

Example 1 outlining the deblocking and purification of the trimer conjugates with a carbonyl linkage 15 and with a succinyl linkage 16. According to the procedure either 24.4 (10 µmol) of dry 13 or 25 mg (10 µmol) of 14 and 190/152 mg (1.25/1 mmol) of DBU in dry $CH_3CN$ (2.5/2 ml) was kept at r.t. for 20/24 h. Then 75/60 mg (1.25/1 mmol) of acetic acid was added to the mixture. The mixture was evaporated and then diluted with 35/20 ml $CHCl_3$, extracted with $H_2O$ (10/2×10 ml) and back-extracted. The organic layer was dried ($MgSO_4$) and evaporated. To the residue was added 80% acetic acid (5 ml). The mixture was kept at r.t. for 19/18 h and then lyophilized. The residue for the carbonyl trimer conjugate 15 was washed and centrifugated several times with $H_2O$ and diethylether to yield 10 mg as a colorless powder. HPLC: 23.95 minutes; FABMS: matrix: DMSO/3-nitrobenzylalcohol 1291 ($MH^+$); $^{252}$Cf-PDMS: accelerating voltage 16 kV, 10 Mio counts: 1291:1 ($MH^+$).

The residue for the succinyl trimer conjugate 16 was washed and centrifugated several times with $H_2O$, $CH_3CN$, diethylether/EtOH 4:1, and diethylether to yield 14 mg as a colorless powder. HPLC: 26.03 minutes.

Preparation of 5'-O-Cholesteryl-Cordycepin Conjugate

In order to prepare a 5'-O-cholesteryl-cordycepin conjugate, Scheme 2, the starting compound 1 was first protected at the 2'-OH group by tert-butyldimethylsilyl chloride ("tbdmsCl") to give 17, followed by detritylation to afford 2'-O-[(tert-butyl)-dimethylsilyl]-6-N-[2-(4-nitrophenyl)ethoxycarbonyl]-cordycepin 18 almost quantitatively. In a one-pot reaction 18 was converted into 5'-O-[2-(cholesteryloxy-carbonyl)ethylcarbonyl]-3'-deoxy-6-N-[2-(4-nitrophenyl)ethoxycarbonyl]-adenosine 20 in three steps; first by treatment with succinic acid anhydride and DMAP to form the corresponding succinyl intermediate which was then esterified by cholesterol to 19 using the carbodiimide method (EDC), and finally the succinyl intermediate was desilylated by fluoride ion in THF and buffered by acetic acid to avoid deblocking the npeoc group. Compound 20 was then deprotected to 5'-O-[2-(cholesteryloxycarbonyl)ethylcarbonyl]-cordycepin 21 by DBU. Alternatively, compound 20 was phosphitylated by bis-N,N-diisopropyl-2(4-nitrophenyl)ethoxyphosphane to the diastereomeric mixture of the phosphoramidite 22, which is an essential building block for the cordycepin trimer formation. The remaining component for this approach was derived from 3'-deoxy-6-N-2'-bis-O-[2-(4-nitrophenyl)ethoxycarbonyl]-adenosine 23 and the phosphoramidite 8 in a normal condensation and oxidation process to form the dimer 24 and, on subsequent detritylation, 25.

The final condensation of 22 and 25 followed by oxidation resulted in the fully blocked trimer conjugate 26. Deprotection of the npe and npeoc groups via β-elimination by DBU and normal work-up with acetonitrile extraction and lyophilization from $H_2O$ led to the conjugate trimer 27. Scheme 2 follows below.

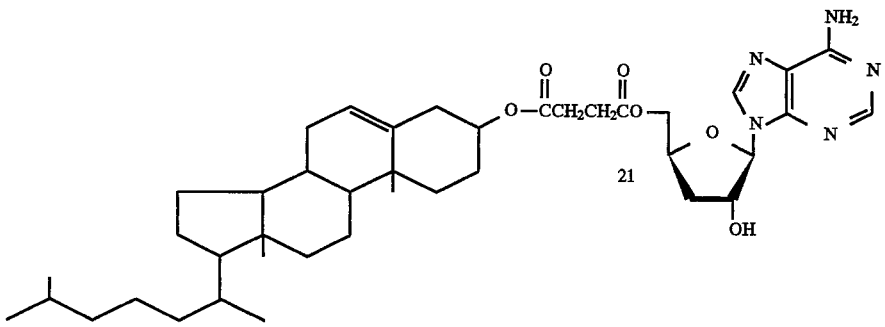

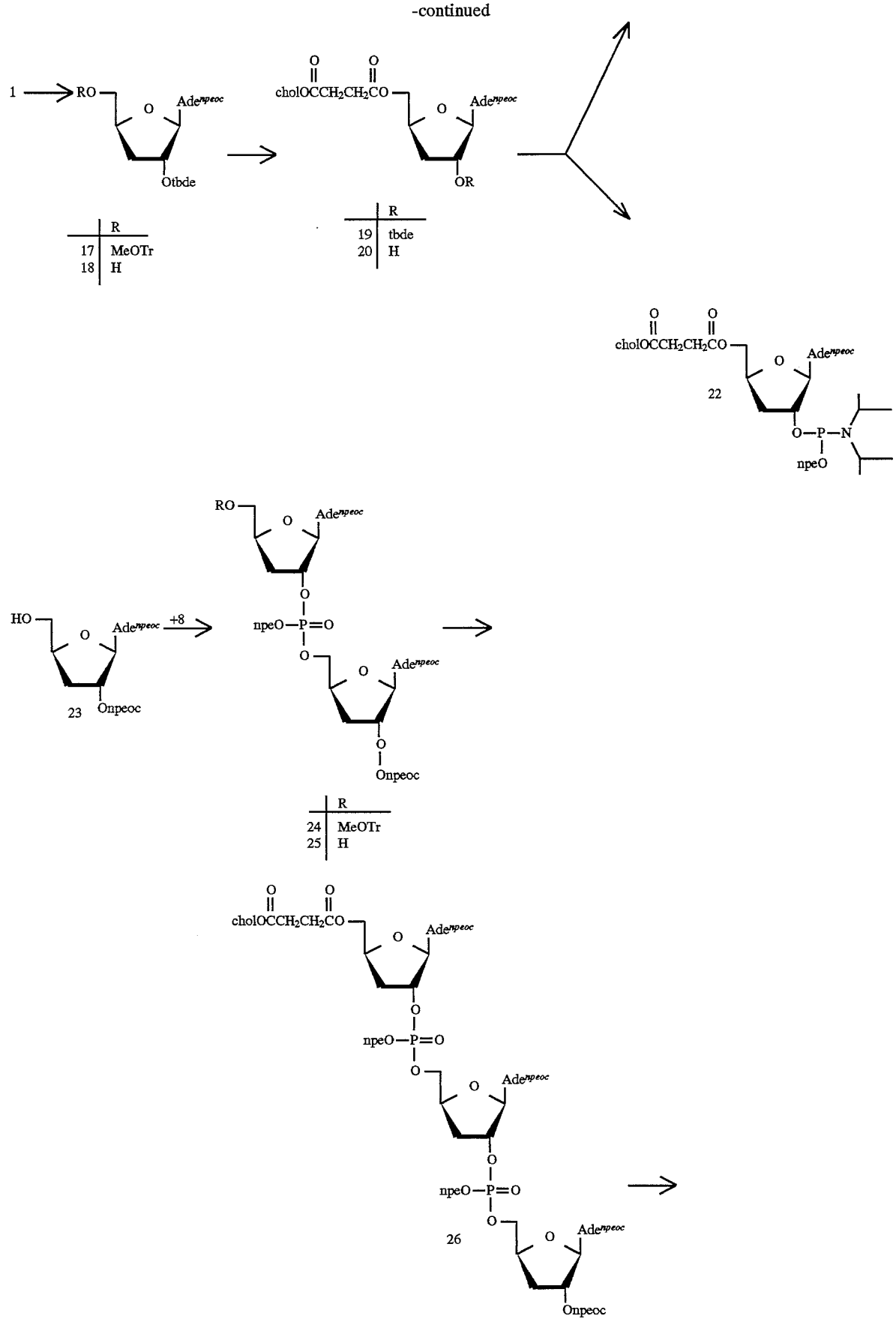

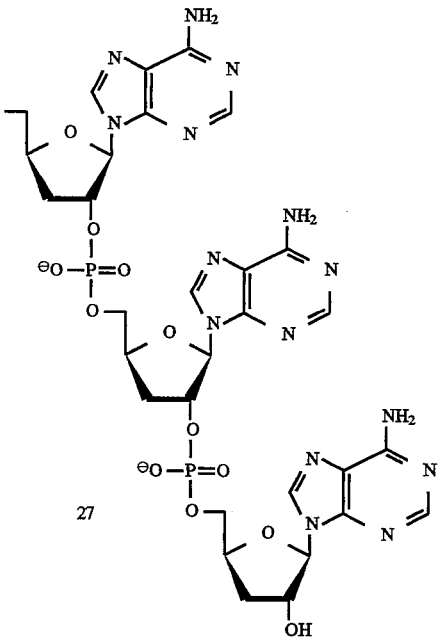

Preparation 11

2'-O-[(tert-Butyl)dimethylsilyl]-3'-deoxy-5'-O-monomethoxytrityl-6-N-[2-(4-nitrophenyl)ethoxycarbonyl]-adenosine 17

A mixture of 2.15 g (3 mmol) of compound 1 and 490 mg (7.2 mmol) of imidazole was coevaporated with absolute pyridine (2×15 ml). The residue was dissolved in absolute pyridine (20 ml) and 543 mg (3.6 mmol) of tbdmsCl was added. The reaction was kept at r.t. for 22 h, diluted with $CHCl_3$ (100 ml), extracted with saturated $NaHCO_3$ solution (3×40 ml) and back-extracted. The organic layer was dried ($MgSO_4$), evaporated and coevaporated with toluene. Purification of the fully protected monomer was by FC (silica gel, gradient toluene/EtOAc 4:1 to toluene/EtOAc 3:1) to give 1.92 g (77%) of 17 as an amorphous solid. UV (MeOH): 273 (sh, 4.40), 267 (4.45), 234 (4.29). $^1$H-NMR ($CDCl_3$): 8.72, 8.25–8.17 (s, m, H—C(8), H—C(2), NH, 2H o to $NO_2$); 7.46–7.23 (m, 14H, 2H m to $NO_2$, MeOTr); 6.83 (d, 2H o to MeO); 6.03 (s, H—C(1')); 4.81 (d, H—C(2')); 4.68 (m, H—C(4')); 4.53 (t, $OCH_2CH_2$(6-N)); 3.79 (s, MeO); 3.48 (dd, H—C(5')); 3.16 (t, $OCH_2CH_2$ (6-N)); 2.19 (m, H—C(3')); 1.95 (m, H—C(3')); 0.90 (s, 9H, t-butyl); 0.14 (s, $CH_3$ at Si); 0.09 (s, $CH_3$ at Si). Anal. calc. for $C_{45}H_{50}N_6O_8Si$ (831.1): C 65.04, H 6.06, N 10.11; found: C 65.28, H 6.16, N 9.80.

Preparation 12

2'-O-[(tert-Butyl)dimethylsilyl]-3'-deoxy-6-N-[2-(4-nitrophenyl)ethoxycarbonyl]-adenosine 18

Detritylation of the fully protected monomer was accomplished by stirring a mixture of 831 mg (1 mmol) of 17 in $CH_2Cl_2$/MeOH 4:1 (20 ml) containing 2% of TsOH×$H_2O$ for 15 minutes at r.t. The mixture was then diluted with EtOAc (130 ml), washed with saturated $NaHCO_3$ solution (2×60 ml) and back-extracted. The organic layer was dried ($MgSO_4$) and evaporated. The residue of the 5'-OH monomer intermediate was purified by FC (silica gel, 11.5×3 cm, gradient toluene/EtOAc 1:1+6% MeOH) to yield 530 mg (95%) of 18 as an amorphous solid. UV (MeOH): 298 (sh, 3.58), 274 (sh, 4.38), 268 (4.44). $^1$H-NMR (($D_6$)DMSO): 10.59 (s, NH); 8.70, 8.61 (2s, H—C(8), H—C(2)); 8.15 (d, 2H o to $NO_2$), 7.61 (d, 2H m to $NO_2$); 5.96 (s, H—C(1')); 5.15 (t, OH—C(5')); 4.74 (m, H—C(2')); 4.38 (m, H—C(4'), $OCH_2CH_2$ (6-N)); 3.73 (m, H—C (5')); 3.58 (m, H—C(5')); 3.10 (t, $OCH_2CH_2$); 2.27 (m, H—C (3')); 1.90 (m, H—C (3')); 0.82 (s, 9H, t-butyl); 0.00 (s, 2×$CH3$ at Si). Anal. calc. for $C_{25}H_{34}N_6O_7Si$ (558.7): C 53.75, H 6.13, N. 15.04; found: C 53.98, H 6.12, N 14.80.

Preparation 13

5'-O-[2-(Cholesteryloxycarbonyl)ethylcarbonyl]-3'-deoxy-6-N-[2-(4-nitrophenyl)-ethoxycarbonyl]-adenosine 20

Analogous to Preparation 3, the partially deprotected monomer was prepared in a one-pot reaction in which a mixture of 560 mg (1 mmol) of 18, 120 mg (1.2 mmol) of succinic acid anhydride, and 160 mg (1.3 mmol) of DMAP in absolute $CH_2Cl_2$ (2.5 ml) was kept at r.t. for 2 hours. The mixture was then esterified by diluting same with 1 ml of absolute $CH_2Cl_2$, and adding 250 mg (1.3 mmol) of EDC and 540 mg (1.4 mmol) of cholesterol. The reaction was kept at r.t. for 1.5 h and diluted with $CHCl_3$ (100 ml), washed with a saturated $NaHCO_3$ solution (2×50 ml) and back-extracted. The organic layer was dried ($MgSO_4$) and evaporated. The crude produce was purified by FC (silica gel, 14×3 cm, gradient toluene/EtOAc 3:2 to toluene/AcOEt 1:1 to toluene/EtOAc 1:1+2% MeOH) to give 824 mg of 19, but which was contaminated with cholesterol as an amorphous solid. This material was desilylated without further purification by treatment in a solution of absolute THF (4 ml) to which a solution of 194 mg (3.2 mmol) of acetic acid in absolute THF (4 ml) and 255 mg (0.80 mmol) of tetrabutylammonium fluoride trihydrate (TBAF) was added. The subsequent mixture was kept at r.t. for 2 days, diluted with EtOAc (160 ml), extracted with a saturated $NaHCO_3$ solution (2×50 ml) and back-extracted. The organic layer was dried ($MgSO_4$) and evaporated. The crude product was again purified by FC (silica gel, 14×3 cm, gradient toluene/EtOAc 1:1+4% MeOH to toluene/EtOAc 1:1+6% MeOH) to give 558 mg (61%) of 20 as an amorphous solid. UV (MeOH): 296 (sh, 3.65), 272 (sh, 4.39), 267 (4.44), 235 (4.30). $^1$H-NMR (($D_6$)DMSO): 10.59 (s, NH); 8.61, 8.52 (2s, H—C(8), H—C(2)); 8.13 (d, 2H o to $NO_2$); 7.60 (d, 2H m to $NO_2$); 5.99 (s, H—C(1')); 5.79 (m, OH—C(2')); 5.25 (m, olef. H at chol.); 4.68 (d, H—C (2')); 4.55 (m, H—C(4')); 4.39–4.23 (m, H—C(3) at chol., $OCH_2CH_2$ (6-N), 2×H—C(5')); 3.09 (t, $OCH_2CH_2$ (6-N)); 2.40–0.59 (m, $CH_2Ch_2$ (succ.), 2×H—C (3'), 43H chol.). Anal. calc. for $C_{50}H_{68}N_6O_1$ (913.2): C 65.76, H 7.51, N 9.20; found: C 65.68, H 7.48, N 9.12.

Preparation 14

5'-O-[2-(Cholesteryloxycarbonyl)ethylcarbonyl]-3'-deoxyadenosine 21

Preparation 14 represents the synthesis of the 5' deprotected monomer conjugate in which 183 mg (0.2 mmol) of the partially protected monomer 20 was coevaporated twice in absolute toluene and added to 0.5 mM DBU in dry pyridine (8 ml). The mixture was stirred at r.t. for 16 h, neutralized with 1M AcOH in pyridine (4 ml) and evaporated. The residue was diluted with $CHCl_3$ (80 ml), extracted with water (3×25 ml) and back-extracted. The organic layer was dried ($MgSO_4$), evaporated and then coevaporated with toluene. The final residue was purified by FC (silica gel, 10×2 cm, gradient $CHCl_3$ to $CHCl_3$+10% MeOH) to give 140 mg (97%) of 21 as an amorphous solid, which was subsequently crystallized in EtOH (8 ml) to give 100 mg (69%) of 21 as colorless crystals. UV (MeOH): 259 (4.13). $^1$H-NMR (($D_6$)DMSO): 8.23, 8.13 (2s, H—C(8), H—C(2)); 7.27 (s, $NH_2$); 5.89 (s, H—C(1')); 5.75 (d, OH—C(2')); 5.29 (m, olef. H at chol.); 4.62 (m, H—C(2')); 4.49 (m, H—C (4')); 4.40 (m, H—C(3) at chol.); 4.24 (m, 2×H—C(5')); 2.52 (m, 4H, $CH_2CH_2$ (succ.)); 2.33–0.63 (m, 45H, 2×H—C(3'), chol.). Anal. calc. for $C_{41}H_{61}N_5O_6$ (720.0): C 68.40, H 8.54, N 9.73; found: C 68.00, H 8.56, N 9.55.

Preparation 15

5'-O-[2-(Cholesteryloxycarbonyl)ethylcarbonyl]-3'-deoxy-6-N-[2-(4-nitrophenyl)-ethoxycarbonyl]-adenosine-2'-[2-(4-nitrophenyl)ethyl N,N-diisopropylphosphoramidite] 22

Alternatively, compound 20 was phosphitylated to form the phosphoramidite 22, which is the primary unit for the trimer conjugate formation. To that end, a mixture of 270 mg (0.295 mmol) of 20, 235 mg (0.59 mmol) of bis (diisopropylamino)-2-(4-nitrophenyl)ethoxyphosphane and 10.3 mg (0.148 mmol) of tetrazole in 1.5 ml dry $CH_3CN$/$CH_2Cl_2$ (2:1) was kept at r.t. for 2.5 h. The reaction mixture was then diluted with $CHCl_3$(30 ml) and extracted with a solution of NaCl/$NaHCO_3$ 3:1 (10 ml) and back-extracted. The organic layer was dried ($MgSO_4$) and evaporated. The phosphoramidite was purified by FC (silica gel, 15×2 cm, toluene/EtOAc 1:1) to give 300 mg (84%) of an amorphous solid. UV ($CH_2Cl_2$): 272 (sh, 4.52), 267 (4.55). $^1$H-NMR ($CDCl_3$): 8.71, 8.20–8.00 (s, m, NH, H—C(8), 4H o to $NO_2$); 7.46–7.26 (m, 4H m to $NO_2$); 6.10 (s, H—C(1')); 5.34 (m, olef. H at chol.); 4.95 (m, H—C(2')); 4.57–4.52 (m, t, H—C(4'), H—C(3) at chol., $OCH_2CH_2$); 3.92–3.75 (m, 2×CH (isopropylamide)); 3.59–3.53 (m, 2×H—C (5')); 3.17 (t, $OCH_2CH_2$); 3.03–2.96 (t, $OCH_2CH_2$); 2.61 (m, $CH_2CH_2$ (succ.)); 2.31–0.67 (m, 57H, 2×H—C(3'), 4×$CH_3$, chol.). Anal. calc. for $C_{64}H_{89}N_6O_{13}P$ (1209.4): C 63.56, H 7.42, N 9.26; found: C 63.15, H 7.60, N 8.97.

Preparation 16

3'-Deoxy-5'-O-monomethoxytrityl-6-N-[2-(4-nitrophenyl)ethoxycarbonyl]-adenylyl-{2'-[$O^P$-(2-(4-nitrophenyl)ethyl]→5'}-3'-deoxy-6-N,2'-O-bis-[2-(4-nitrophenyl)ethoxycarbonyl]-adenosine 24

The 5' fully protected dimer was formed from the condensation of a mixture of 277 mg (0.43 mmol) of 3'-deoxy-6-N-2'-O-bis[2-(4-nitrophenyl)ethoxycarbonyl]-adenosine 23, prepared according to the method of Charubala et al., *Helv. Chim. Acta* 70: 2028–2038 (1987), 880 mg (0.87 mmol) of the phosphoramidite 8, and 152 mg (2.17 mmol) of tetrazole stirred in absolute $CH_3CN$ (3 ml) and absolute $CH_2Cl_2$ (0.2 ml) under nitrogen at r.t. for 2 h. The condensate was oxidized with a solution of $I_2$ (500 mg $I_2$, 3 ml pyridine, 1 ml $CH_2Cl_2$, 1 ml $H_2O$) until no color change was detected. The mixture was stirred for 15 minutes and then diluted with 100 ml $CHCl_3$, washed with a solution of $Na_2S_2O_3$/NaCl (2×30 ml) and back-extracted. The organic layer was dried (MgSO4), evaporated and coevaporated with toluene. Purification of the residue was by FC (silica gel, 13×3 cm, gradient toluene/EtOAc 1:1+4% MeOH to toluene/EtOAc 1:1+20% MeOH) to give 320 mg (47%) of 24 and 306 mg (45%) of an impure fraction as an amorphous solid. UV (MeOH): 272 (sh, 4.78), 267 (4.82), 236 (sh, 4.46). $^1$H-NMR ($CDCl_3$): 8.68–8.60, 8.24–8.02 (4s, m, 2×NH, 2×H—C(8), 2×H—C(2), 4×2H o to $NO_2$); 7.46–7.16 (m, 4×2H m to $NO_2$, 12H MeOTr); 6.80 (d, 2H o to MeO); 6.18 (d, H—C (1')); 5.62 (m, H—C(2')); 5.42 (m, H—C(2')); 4.60–4.25 (m, 2×H—C(4'), 4×$OCH_2CH_2$, 2×H—C(5')); 3.78 (s, MeO); 3.46 (m, H—C(5')); 3.32 (m, H—C (5')); 3.20–3.02 (m, 4×$OCH_2Ch_2$); 2.70 (m, H—C(3')); 2.50 (m, H—C(3')); 2.27 (m, H—C(3')); 2.21 (m, H—C(3')). Anal. calc. for $C_{75}H_{69}N_{14}O_{23}P$×½toluene (1611.6): C 58.51, H 4.57, N 12.16; found: C 58.38, H 4.63, N 11.83.

Preparation 17

3'-Deoxy-5'-O-monomethoxytrityl-6-N-[2-(4-nitrophenyl)ethoxycarbonyl]-adenylyl-{2'-[$O^P$-(2-(4-nitrophenyl)ethyl)]→5'}-3'-deoxy-6-N-2'-O-bis-[2-(4-nitrophenyl)ethoxycarbonyl]-adenosine 25

Analogous to the detritylation of the fully protected monomer outlined in Preparation 12, the fully protected dimer was detritylated by a mixture of 320 mg (0.2 mmol) of 24 stirred in $CH_2Cl_2$/MeOH 4:1 (4 ml) containing 2% of TsOH ×$H_2O$ for 1 h at r.t. The resulting mixture was diluted with $CHCl_3$ (40 ml), washed with a saturated $NaHCO_3$ solution (2×20 ml) and back-extracted. The organic layer was dried ($MgSO_4$) and evaporated. The residue of the 5'-OH dimer intermediate was purified by FC (silica gel, 12×2 cm, gradient $CHCl_3$+1% MeOH to $CHCl_3$+10% MeOH) to yield 225 mg (85%) of an amorphous solid. UV (MeOH): 296 (sh, 4.20), 272 (sh, 4.80), 267 (4.84). $^1$H-NMR (($D_6$)DMSO): 10.06 (m, 2×NH); 8.61–7.36 (m, 2×H—C(8), 2×H—C(2), 4×2H o to $NO_2$, 4×2H m to $NO_2$); 6.18 (m, 2×H—C(1')); 5.61 (m, H—C(2')); 5.24 (m, H—C (2')); 5.11 (m, OH—C(5')); 4.40–4.04 (m, 2×H—C(4'), 4×$OCH_2CH_2$, 2×H—C(5')); 3.65 (m, H—C(5')); 3.44 (m, H—C(5')); 3.09 (m, 3×$OCH_2CH_2$); 2.90 (m, $OCH_2CH_2$); 2.60 (m, H—C(3')); 2.26 (m, 2×H—C(3')); 2.05 (m, H—C (3')). Anal. calc. for $C_{55}H_{53}N_{14}O_{22}P$ ×$H_2O$ (1311.0): C 50.39, H 4.23, N 14.96; found: C 50.47, H 4.25, N 14.54.

Preparation 18

5'-O-[2-(Cholesteryloxycarbonyl)ethylcarbonyl]-3'-deoxy-6-N-[2-(4-nitrophenyl)-ethoxycarbonyl]-adenylyl-{2'-[$O^P$-(2-(4-nitrophenyl)ethyl)]→5'}-3'-deoxy-6-N-[2-(4-nitrophenyl)ethoxycarbonyl]-adenylyl-{2'-[$O^P$-(2-(4-nitrophenyl)ethyl)]→5'}-3'-deoxy-6-N-2'-O-bis-[2-(4-nitrophenyl)ethoxycarbonyl]-adenosine 26

Following the same procedure outlined in Preparation 16, 171 mg (0.133 mmol) of 25, 242 mg (0.2 mmol) of 8, and 47 mg (0.665 mmol) of tetrazole were stirred in anhydrous $CH_3CN$ (1 ml) and anhydrous $CH_2Cl_2$ (0.2 ml) under nitrogen at r.t. for 8 h. The condensate was treated identically to that of Preparation 16 through the purification phase, except that the mixture was washed twice with 15 ml of a $Na_2S_2O_3$/NaCl solution. The 5' fully protected trimer conjugate was purified by FC (silica gel, 13×2 cm, gradient $CHCl_3$ to $CHCl_3$+4% MeOH) to give 42 mg (13%) of an amorphous solid. The remaining 210 mg of impure product had to be purified by prep. TLC (silica gel, 20×40 cm, $CHCl_3$+5% MeOH) to give 125 mg (39%) of 26 and 63 mg (43%) of the educt 25. UV ($CH_2Cl_2$): 285 (sh, 4.73), 272 (sh, 4.99), 267 (5.03). $^1$H-NMR ($CDCl_3$): 8.92–7.94 (m, 3×H—C(8), 3×H—C(2), 6×2H o to $NO_2$); 7.48–7.27 (m, 6×2H m to $NO_2$); 6.14–6.06 (m, 3×H—C(1')); 5.66–5.31 (m, 3×H—C(2'), olef. H at chol.); 4.59–4.10 (m, 3×H—C(4'), H—C(3) at chol., 6×$OCH_2CH_2$, 6×H—C(5')); 3.17–3.02 (m, 6×$OCH_2CH_2$); 2.59 (b, $CH_2CH_2$ (succ.)); 2.30–0.66 (m, 6×H—C(3'), 43H chol.). Anal. calc. for $C_{113}H_{127}N_{21}O_{36}P_2$×$H_2O$ (2435.3): C 55.73, H 5.34, N 12.08; found: C 55.44, H 5.40, N 11.86.

EXAMPLE 2

5'-O-[2-(Cholesteryloxycarbonyl)ethylcarbonyl]-3'-deoxyadenylyl-(2'→5')-3'-deoxy-adenylyl-(2'→5')-3'-deoxyadenosine 27

The 5'-O-cholesteryl-cordycepin conjugate was finally formed via acetonitrite extraction followed by lyophilization utilizing a mixture of 27 mg (11 μmol) of dry 26 and 20 mg (133 μmol) of DBU in dry $CH_3CN$ (0.5 ml) which had been kept at r.t. for 2 days. After the two days elapsed, 4 drops of acetic acid were added and the mixture was evaporated. The residue was washed multiple times with $CH_3CN$ and lyophylised. The product 27 (12 mg) was obtained as a colorless powder. HPLC: 24.69 minutes; FABMS: matrix: DMSO/3-nitrobenzylalcohol 1347 ($MH^+$).

In the case where the $R_2$ group of all internucleotide bonds (Formula I) of the molecule comprise oxygen, i.e., the linkages comprise phosphodiester bonds, the 5'-monophosphates are readily prepared by reacting the corresponding unphosphorylated core compound with $POCl_3$. In the case wherein at least one internucleotide linkage comprises a phosphorothioate bond, i.e., $R_2$=sulfur, such treatment would result in the elimination of sulfur from the phosphorothioate internucleotide linkage, and the formation of a 2',5'-oligoadenylate. Thus, the 5'-monophosphates of phosphorothioate bond-containing core oligomers must be prepared from the corresponding fully protected core oligomer from which the monomethoxytrityl blocking groups on the 5'-terminal nucleotide has been removed. The procedure is described in detail in U.S. Pat. No. 4,924,624, columns 26 through 31 thereof, which is incorporated by reference herein.

Preparation of the 5'-Monophosphate of 2',5'-Cordycepin-Cholesterol

The 5'-monophosphates of the unphosphorylated core cholesterol conjugates of the present invention may be prepared from the fully blocked trimers, 13 and 14 by detritylation with acid treatment, followed by reaction with di-p-nitrophenylethylphosphoryl chloride. Further deblocking and chromatography results in isolation of the 5'-monophosphate oligomers. The 5'monophosphorylation procedure may be carried out according to the method set forth in Example 3 below.

EXAMPLE 3 a. 5'-O-phosphoryl-3'-deoxyadenylyl-(2'→5')3'-deoxyadenylyl-(2'→5')-2'-O-cholesterylcarbonyl-3'-deoxyadenosine b. 5'-O-phosphoryl-3'-deoxyadenylyl-(2'→5')3'-deoxyadenylyl-(2'→5')-2'-O-[2-(cholesteryloxycarbonyl)ethylcarbonyl-3'-deoxyadenosine To prepare the 5'-monophosphate of the trimer conjugate, 0.1 mM of the fully protected trimer 13 or 14, prepared according to Preparation 10 above, is treated with 2 ml of a solution of 2% p-toluenesulfonic acid in dichloromethane/methanol (7/3, v/v) for 30 minutes at room temperature to remove the monomethoxytrityl group. Purification by silica gel chromatography on a preparative plate with chloroform/methanol (95/5, v/v) gives a 90% yield of the 5'-deprotected analog.

The product is then dissolved in one liter of absolute pyridine and treated with 0.27 mmole of di-p-nitrophenylethylphosphoryl chloride, as described by Himmelsbach et al., 23: 4793 (1982), for 1 hr at room temperature. After dilution with 25 ml of chloroform, the reaction mixture is extracted three times with a phosphate buffer of pH 7. The organic layer is dried over sodium sulfate, filtered, evaporated and coevaporated three times with 10 ml of toluene each time. The residue is purified by silica gel chromatography on preparative plates in chloroform/methanol (9/1, v/v) to give an 80% yield in the form of an amorphous solid.

0.01 Mmole of the latter material is treated after several evaporations with absolute pyridine in 10 ml of a 0.5M solution of diazabicyclo[4.3.0]undecene in absolute pyridine and stirred for 36 hours at room temperature to cleave the p-nitrophenylethyl groups by β-elimination. Purification and isolation of the trimer core 5'-monophosphate was achieved by DEAE-Sephadex chromatography and lyophilization of the main fraction.

Preparation of 5'-Diphosphates and 5'-Triphosphates OF 2',5'-Cordycepin-Cholesterol CONJUGATES The 5'-diphosphates and 5'-triphosphates of the core molecules may be prepared according to the procedure set forth in U.S. Pat. No. 4,859,768. Briefly, they may be prepared by adding 0.5 mM of tributylammonium pyrophosphate dissolved in 5 ml of dimethylformamide to 0.1 mM of monophosphorylated core as the anhydrous tributylammonium salt in 1 ml of dimethylformamide and 0.5 mM of 1,1'-carbonyldiimidazole. After 20 hours at room temperature, the reactants are treated with 5 ml of methanol, evaporated to dryness and chromatographed on a 2×20 cm DEAE cellulose column. The 5'-di and triphosphates are isolated following a linear gradient (0–0.4M in 3 1 at pH 7.5) of triethylammoniumbicarbonate. This is the method of Hoard, et al., J. Amer. Chem. Soc. 87: 1785–1788 (1965), which is incorporated herein by reference. The 5'-diphosphates and 5'-triphosphates may then be purified by DEAE-Sephadex®.

EFFECT OF CORDYCEPIN-CHOLESTEROL CONJUGATES ON INHIBITION OF HIV-1-INDUCED SYNCYTIA FORMATION

The infected centers assay as described by Henderson et al., *Virology* 182: 186–198 (1994), was used to measure the ability of the 2',5'-oligoadenylate-cholesterol derivatives to inhibit HIV-1 induced syncytia formation, an indicator of HIV-1 replication in T cells. Freshly isolated peripheral blood lymphocytes (PBL) were treated with 2-5A or derivatives for 2 h and infected with HIV-1 strain IIIB at a modality of infection (m.o.i.) of approximately 0.1. The infected PBL were maintained in RPMI-1640 medium supplemented with 10% (v/v) heat-in-activated fetal calf serum at 37° C. in a humidified 5% $CO_2$ in air atmosphere. After 48 h, the cells were washed twice in Hank's balanced salt solution, serially diluted and seeded into multiple wells of a 96-well microtiter plate. Immediately, $2 \times 10^5$ exponentially growing Sup T1 cells were added to each well; Sup T1 cells readily form a syncytium with a cell which is productively infected with HIV-1. The wells were examined daily for the presence of syncytia, using a tissue culture microscope. The first signs of syncytia formation can be seen in 12 h, with some complete syncytia developing by 24 h. Final results were read at 96 h. Each syncytium was counted as a single infected cell. The number of syncytia per seeded cell is determined and expressed as an infected center per infected cell. In the control (no 2-5A derivative added), 100% syncytia formation was equivalent to 12±3 syncytia per 200 HIV-1 infected cells.

Authentic 2-5A trimer core inhibited syncytia formation nine-fold, whereas cordycepin trimer core inhibited syncytia formation eighteen-fold. Both cordycepin-cholesterol trimer conjugates 16 and 27 were significantly more potent inhibitors of HIV-1 induced syncytia formation (333-fold and 1,000-fold, respectively) than the cordycepin trimer core (Table 1). The 5'-cordycepin-cholesterol conjugate 27 had the highest activity and inhibited HIV-1 induced syncytia formation 18,000-fold. Neither DMSO, cholesterol, cordycepin nor adenine exhibited any inhibitory activity. Without wishing to be bound by any theory, it would appear that the increased anti-HIV-1 activity of the cordycepin cholesteryl conjugates relative to cordycepin trimer core is attributed to increased cellular uptake via membrane fluidization or by receptor-mediated endocytosis.

Again, without wishing to be bound by any theory, it is believed that the unexpected efficacy of the conjugate having the cholesterol moiety attached to the 5'-terminal nucleoside (hereinafter the "5'-conjugate") may be attributable to more than enhanced uptake. It is believed that the 5'-conjugate may be acting not merely as a prodrug for the corresponding core 2'-5' cordycepin oligomer, but as a unitary new drug. It is believed that the cholesterol moiety may not be hydrolyzed upon absorption into the cellular membrane, i.e., it is not cleaved from the oligonucleotide, and that in fact the biological effect of the 5'-conjugate may be the result of an intact molecule.

TABLE 1

Inhibition of HIV-1 replication in peripheral blood lymphocytes by cordycepin - cholesterol conjugates

| Test compound[1] | Syncytia/plated cell (m.o.i. (IIIB) = 0.10) | Fold reduction in infection |
|---|---|---|
| control (vehicle) | 18/200 | 1 |
| 2-5A trimer core | 2/200 | 9 |
| cordycepin trimer core | 1/200 | 18 |
| cordycepin - cholesterol trimer conjugate 16 | 3/200,000 | 6,000 |
| cordycepin - cholesterol trimer conjugate 27 | 1/200,000 | 18,000 |
| DMSO (control) | 20/200 | 0.9 |
| cholesterol | 10/200 | 1.8 |
| cordycepin | 12/200 | 1.5 |
| adenine | 14/200 | 1.3 |

[1]Compounds were tested at 100 µM, with the exception that cordycepin and adenine were tested at 300 µM and DMSO was tested at 1.7%.

For pharmaceutical use, the compounds of the invention may be taken up in pharmaceutically acceptable carriers, such as, solutions, suspensions, tablets, capsules, ointments, elixirs and injectable composition and the like. They are administered to subjects suffering from viral infection. The dosage administered depends upon the nature and severity of the infection, the disease stage, and, when administered systematically, the size and weight of the infected subject.

The compounds are generally administered in the form of water-soluble salts. Pharmaceutically acceptable water soluble salts include, for example, the sodium, potassium or ammonium salts of the active compounds. They are readily dissolved in water or saline solution. Thus, the preferred formulation for pharmacological use comprises a saline solution of the desired compound in salt form. The formulation may further contain an agent, such as a sugar or protein, to maintain osmotic balance. The salt form of the compound is preferred owing to the relatively high acidity (about pH 3) of the acid form of the compounds.

The compounds of the invention may be used as a treatment or prophylactically for humans and animals from viral infectives such as Herpes simplex, rhinovirus, hepatitis and other infections of the hepatitis virus family, Epstein Barr virus, measles virus, multiple sclerosis (which may be caused by a viral agent) and the various Human Immunodeficiency Viruses ("HIV"), such as HIV-1, which causes cutaneous T cell lymphoma, HIV-2, which causes Sezary lymphoma, and HIV-3, which is responsible for Acquired Immune Deficiency Syndrome ("AIDS"). The compounds of the invention inhibit the HIV-1 Induced Syncytia formation.

The compounds may be applied topically to treat skin cancers caused by radiation, carcinogens or viral agents. Such skin cancers include cutaneous T-cell lymphoma, Sezany lymphoma, Xeroderma pigmentosium, ataxia telangiectasia and Bloom's syndrome. A sufficient amount of a preparation containing a compound of the invention is applied to cover the lesion or affected area. An effective concentration of active agent is between about $10^{-3}$M and $10^{-5}$M, with $10^{-4}$M being preferred.

The compounds of the present invention may also be used to treat plant-infecting virus, particularly tobacco mosaic virus, and other viruses which cause necrosis in turnips, cucumber, orchids and in other plants. Such viruses include, but are not limited to, tobacco vein mottling virus, vesicular stomatitis virus, vaccinia virus, turnip necrosis virus, and cymbidium orchid virus.

The compounds may be administered effectively to plants by topical application by abrasion of the leaf surface, aerosol spray, treatment of the soil, spraying, or dusting.

An effective antiviral composition may be formed by combining one or more of the compounds of the invention with a carrier material suitable for agricultural use. While the individual stereoisomers are preferred for pharmaceutical use, mixtures of one or more of stereoisomers may be employed in agricultural applications. The active compound may also be administered by spraying insect vectors such as aphids, thrips and whiteflies which carry virus to plants. The dosage administered depends upon the severity of the infection.

The compounds of the invention may be applied to plant seeds prior to germination to control viruses contained in the germ plasm. The seeds may be soaked in a solution of polyethylene glycol ("PEG") containing one or more of the compounds. PEG brings the seeds to physiological activity and arrest. The relative concentration of active compound to PEG depends upon the type of seed under treatment.

Plants may be effectively treated with an aqueous formulation containing from about $10^{-1}$ to about $10^{-2}$M concentration of active ingredient. The compounds of the invention may be applied at very low concentrations. An effective amount of active ingredient on the plant surface is from about $10^{-8}$ to about $10^{-12}$ mole per $cm^2$ of plant surface area, with about $10^{-10}$ mole to about $10^{-12}$ mole per $cm^2$ being preferred. For the typical tobacco plant of 1,000 $cm^2$, $10^{-5}$M of compound is effective. At this rate, one pound of active ingredient is sufficient to treat $2\times10^8$ tobacco plants.

For agricultural application, the compounds are advantageously administered in the form of water-soluble salts, e.g. ammonium or potassium salts. Sodium salts are generally avoided in treating edible plants.

The compounds of the invention are readily dissolved in water, particularly at such low concentrations. Aqueous formulations for agricultural use may optionally contain a sticker and/or a UV-stabilizer. Such agents are well-known to those skilled in the art. Fatty acids (1%) are useful as spreader sticker agents. Effective UV-stabilizers include, for example, p-aminobenzoic acid.

For antiviral use in mammals, the compounds of the invention are administered parenterally, such as intravenously, intraarterially, intramuscularly, subcutaneously, or when administered as anti-cancer agents, intratumorally. The preferred route of administration for antiviral therapy is intravenous injection. The compounds of the invention may be administered to mammals at very low concentrations. The actual dosage administered may take into account the size and weight of the patient, whether the nature of the treatment is prophylactic or therapeutic in nature, the age, health and sex of the patient, the route of administration, the nature and stage of the affliction, and other factors. An effective daily dosage of active ingredient is from about 25 pg per 70 kg of body weight (approximately 152 lbs) to about 2.5 g per 70 kg of body weight. Greater or lower dosages may be utilized, depending on the need. The preferred daily dosage is about 0.5 g per 70 kg of body weight. If administering a compound such as the 5'-cholesterol cordycepin trimer conjugate, compound 27, given that it is a 1000 times more potent than other 2-5A analogs, the amount to be administered may be reduced accordingly. A preferred daily dosage of the latter compound is about 25 pg per 70 kg of body weight. Those skilled in the art should readily be able to derive appropriate dosages and schedules of aministration to suit the specific circumstance and needs of the patient.

It is expected that an effective treatment regimen would include administration of the daily dosage for two days. Treatment would continue at least until the disease condition is substantially abated.

Preferably, the therapeutic end point is determined by testing for the continued presence of viral DNA. Such testing can be done by polymerase chain reaction (PCR) in which the presence of viral DNA is assayed according to now conventional nucleic acid amplification techniques. PCR primers of appropriate nucleotide sequences for amplification of viral DNA can be prepared from known viral nucleotide sequences. To obtain DNA for testing, patient peripheral blood mononuclear cells are lysed with an appropriate lysing agent, such as NP-40.

Alternatively, testing for the continued presence of the virus can be performed by an antigen-antibody assay using any of the known monoclonal or polyclonal antisera against a protein antigen of the target virus' protein coat. For example, an antigen-antibody assay may be employed to detect any of the protein antigen in the antigens HIV protein coat, for example, the gp120, p17 or p24. Moreover, the target antigen is not limited merely to coat protein antigens. Antisera can be targeted against a suitable non-coat protein antigen, such as the HIV reverse transcriptase (RT) molecule. Monoclonal antibodies to HIV RT are known. Sobol et al., *Biochemistry* 30: 10623–10631 (1991).

Additionally, testing for the presence of the infecting virus during or post-treatment could be accomplished by an assay which assesses the viral load in the patient's blood stream. This can be done by determining the level of syncytia formation, i.e., by measuring the formation of viral particles. See procedure outlined in Henderson et al., *Virology* 182: 186–198 (1994).

In addition to administration with conventional carriers, the compounds of the present invention may be administered by a variety of specialized oligonucleotide or nucleic acid delivery techniques. 2-5A and its analogues have been successfully encapsulated in various encapsulating materials, such as in unilamellar liposomes and delivered with the aid of monoclonal antibodies to cells, Bayard et al., *Eur. J. Biochem.* 151: 319–325 (1985). Reconstituted Sendai virus envelopes have been successfully used to deliver RNA and DNA to cells, Arad et al., *Biochem. Biophys. Acta.* 859: 88–94 (1986). Moreover, the virus envelope is not limited to Sendai virus, but could include encapsulation in any retroviral amphotrophic particle. For example, an HIV envelope could be formed from any part or all of the outer protein coat of a non-infectious HIV particle. Such particles as gp 120 can be cloned by known recombinant techniques. These techniques may be utilized for introduction of the present compounds into cells, to augment the uptake-enhancing effect of the cholesteryl moiety. It is further contemplated that the compounds of the invention may be administered in the form of prodrugs in which lipophilic groups are attached to, for example, the 5'-terminal hydroxyl group of the core compound.

All references with respect to synthetic, preparative and analytic procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:
1. A compound of the formula:

[Structural formula showing adenine nucleotide trimer with R₁, R₂, R₃, R₄, R₅ substituents]

wherein:

n is an integer from 1 to 8;

R₁ is selected from the group of consisting of T, T' and Y, wherein

T is

[Cholesteryl carbonate structure: O—C(=O)—O—cholesteryl]

T' is

[Structure: O—C(=O)—(CH₂)ₓ—C(=O)—O—cholesteryl]

where x is an integer from 1 to 18;

Y is $$HO \left[ \begin{matrix} O \\ | \\ P-O \\ \| \\ O \end{matrix} \right]_m$$

where m is zero, 1, 2, or 3;

each R₂ is independently selected from the group consisting of oxygen and sulfur;

each R₃ is independently selected from the group consisting of hydrogen and hydroxyl;

R₄ is selected from the group consisting of hydrogen, hydroxyl, T and T';

R₅ is selected from the group consisting of hydrogen, hydroxyl, T and T';

provided that all R₁, R₄ and R₅ may not be T or T';

at least one R₃ is hydrogen or R₄ is hydrogen; and at least one of R₁, R₄ and R₅ must be T or T';

or a water soluble salt thereof.

2. A compound according to claim 1 wherein each R₃ is hydrogen and R₄ is hydrogen.

3. A compound according to claim 2 wherein each R₂ is oxygen.

4. A compound according to claim 3 where n is 1 or 2 and R₅ is T; or a water soluble salt thereof.

5. A compound according to claim 3 where n is 1 or 2 and R₁ is T; or a water soluble salt thereof.

6. A compound according to claim 3 where n is 1 or 2 and R₅ is T'; or a water soluble salt thereof.

7. A compound according to claim 3 where n is 1 or 2 and R₁ is T'; or a water soluble salt thereof.

8. A compound according to any of claims 4, 5, 6 or 7 wherein n is 1.

9. A compound according to claim 1 wherein R₁ is Y and m is zero.

10. A compound according to claims 6 or 7 where x is 2.

11. A compound according to claim 1 which is 3'-deoxyadenylyl-(2'→5')-3'-deoxyadenylyl-(2'→5')-2'-O-(2-cholesterylcarbonyl)ethylcarbonyl-3'-deoxyadenosine; or a water soluble salt thereof.

12. A compound according to claim 1 which is 5'-O-[2-(cholesteryloxycarbonyl)ethylcarbonyl]-3'-deoxyadenylyl-(2'→5')-3'-deoxyadenylyl-(2'→5')-3'-deoxyadenosine; or a water soluble salt therof.

13. An antiviral composition comprising a compound according to claim 1 in combination with a pharmaceutical carrier.

14. A method of treating viral infection in a mammal comprising administering thereto an antiviral effective amount of a compound according to claim 1.

15. A method of treating viral infection in a plant comprising administering thereto an antiviral effective amount of a compound according to claim 1.

16. An antiviral composition comprising a compound according to claim 1 in combination with an agricultural carrier.

* * * * *

UNITED STATES PATENT AND TRADEMARK OFFICE
CERTIFICATE OF CORRECTION

PATENT NO. : 5,643,889
DATED : July 1, 1997
INVENTOR(S) : Robert J, Suhadolnik, et. al.

It is certified that error appears in the above-identified patent and that said Letters Patent is hereby corrected as shown below:

Title page, item [73], change the Assignee information to --Temple University - Of The Commonwealth System of Higher Education--.

Signed and Sealed this

Second Day of June, 1998

Attest:

BRUCE LEHMAN

Attesting Officer

Commissioner of Patents and Trademarks